US011617649B2

(12) United States Patent
O'Connell et al.

(10) Patent No.: US 11,617,649 B2
(45) Date of Patent: Apr. 4, 2023

(54) TRANSCATHETER DELIVERY SYSTEMS AND DELIVERY CATHETERS FOR PROSTHETIC MITRAL VALVE DELIVERY, AND METHODS FOR PROSTHETIC MITRAL VALVE DELIVERY USING A RETROGRADE APPROACH

(71) Applicant: MEDTRONIC VASCULAR, INC., Santa Rosa, CA (US)

(72) Inventors: Barry O'Connell, Galway (IE); Patrick Griffin, Galway (IE); Michael Bateman, St. Louis Park, MN (US); William Haynes, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 385 days.

(21) Appl. No.: 16/903,484

(22) Filed: Jun. 17, 2020

(65) Prior Publication Data
US 2020/0306039 A1 Oct. 1, 2020

Related U.S. Application Data

(63) Continuation of application No. 15/411,542, filed on Jan. 20, 2017, now Pat. No. 10,716,667.

(51) Int. Cl.
*A61F 2/24* (2006.01)

(52) U.S. Cl.
CPC .......... *A61F 2/2433* (2013.01); *A61F 2/2436* (2013.01); *A61F 2/2466* (2013.01)

(58) Field of Classification Search
CPC .... A61F 2/2436; A61F 2/2409; A61F 2/2418; A61F 2/243; A61F 2/2427; A61F 2/24; A61F 2/2433; A61F 2/2466
See application file for complete search history.

(56) References Cited

U.S. PATENT DOCUMENTS 8,831,741 B2 * 9/2014 Griswold .......... A61M 25/0074
607/116
2001/0047138 A1 11/2001 Kokate et al.
(Continued)

FOREIGN PATENT DOCUMENTS

WO 2016108181 A1 7/2016
WO 2016149543 A1 9/2016

OTHER PUBLICATIONS

International Search Report and Written Opinion dated Feb. 21, 2018, International Application No. PCT/US2017/063714.

*Primary Examiner* — Tuan V Nguyen
(74) *Attorney, Agent, or Firm* — Medler Ferro Woodhouse & Mills PLLC

(57) ABSTRACT

Transcatheter delivery systems, delivery catheters and associated methods for percutaneous delivery of prosthetic mitral valves using a retrograde approach are disclosed herein. A heart valve delivery system configured in accordance herewith includes a delivery catheter having an elongated tubular component and an articulation assembly at a distal end thereof. The articulation assembly includes an arm portion coupled to the tubular component by an elbow or hinge portion. In a closed, delivery state, the elbow portion positions the arm portion generally parallel to the tubular component for delivery of the delivery catheter through the vasculature. In an open, deployed state, the elbow portion positions the arm portion in a non-axial direction with respect to a longitudinal axis of the tubular component for orienting and positioning a prosthetic valve device carried by the arm portion, e.g., within the native mitral valve region.

20 Claims, 26 Drawing Sheets

(56) References Cited

U.S. PATENT DOCUMENTS

| | | |
|---|---|---|
| 2005/0137622 A1 | 6/2005 | Griffin |
| 2006/0004439 A1 | 1/2006 | Spenser et al. |
| 2007/0249999 A1 | 10/2007 | Sklar et al. |
| 2009/0234443 A1 | 9/2009 | Ottma et al. |
| 2010/0286768 A1 | 11/2010 | Alkhatib |
| 2012/0041533 A1* | 2/2012 | Bertolino ................ A61F 2/966 |
| | | 623/1.11 |
| 2012/0197193 A1 | 8/2012 | Krolik et al. |
| 2012/0209375 A1* | 8/2012 | Madrid ................ A61F 2/2427 |
| | | 604/95.04 |
| 2013/0261738 A1 | 10/2013 | Clague et al. |
| 2013/0297012 A1* | 11/2013 | Willard ................ A61F 2/2427 |
| | | 623/2.11 |
| 2013/0297013 A1 | 11/2013 | Klima et al. |
| 2014/0330368 A1 | 11/2014 | Gloss et al. |
| 2015/0073539 A1 | 3/2015 | Geiger et al. |
| 2016/0095703 A1 | 4/2016 | Thomas et al. |

* cited by examiner

TRANSCATHETER DELIVERY SYSTEMS AND DELIVERY CATHETERS FOR PROSTHETIC MITRAL VALVE DELIVERY, AND METHODS FOR PROSTHETIC MITRAL VALVE DELIVERY USING A RETROGRADE APPROACH

CROSS-REFERENCE TO RELATED APPLICATION

This application is a continuation of prior U.S. application Ser. No. 15/411,542, filed Jan. 20, 2017, now U.S. Pat. No. 10,716,667, which is hereby incorporated by reference in its entirety for all purposes.

FIELD OF THE INVENTION

The present technology relates generally to intravascular delivery of prosthetic mitral valves using a retrograde approach, delivery catheters for mitral valve prosthesis delivery and associated systems and methods. In particular, several embodiments are directed to delivery catheters suitable for crossing an aortic valve for delivery of a mitral valve prosthesis.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To ensure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Prosthetic heart valves have been developed for repair and replacement of diseased and/or damaged heart valves. Such valves can be percutaneously delivered and deployed at the site of the diseased heart valve through catheter-based systems. Such prosthetic heart valves can be delivered while in a low-profile or compressed/contracted arrangement so that the prosthetic valves can be advanced through the patient's vasculature. Once positioned at the treatment site, the prosthetic valves can be expanded to engage tissue at the diseased heart valve region to, for instance, hold the prosthetic valve in position. While these prosthetic valves offer minimally invasive methods for heart valve repair and/or replacement, challenges remain to providing effective and less invasive prosthetic valve delivery systems, particularly for mitral valve replacement. For example, catheter delivery approaches and techniques for mitral valve replacement have largely utilized a transseptal approach; however, challenges, such as catheter positioning of a heart valve prosthesis in the native mitral valve and size limitations of the catheter that can be successfully delivered via inter-atrial septum puncture, limit both the feasibility of heart valve prosthetic delivery as well as the size of the heart valve prosthesis. Other delivery routes for mitral valve replacement, such as a retrograde approach and trans-apical puncture, have also presented difficulties in precise positioning of heart valve devices and in avoiding injury to myocardium tissue in the left ventricle.

BRIEF SUMMARY OF THE INVENTION

Embodiments hereof are directed to transcatheter delivery systems and catheter assemblies for delivering prosthetic heart valves and methods for percutaneous delivery of a prosthetic heart valve device to the mitral valve of a patient using a retrograde approach. In particular, the delivery systems and catheter assemblies are suitable for accessing the mitral valve and orienting the prosthetic heart valve device by an approach from the aortic arch, across the aortic valve, and into the left ventricle. In an embodiment, a heart valve prosthesis delivery system can include a delivery catheter comprising i) an elongated tubular component, ii) an arm portion, and iii) an elbow or hinge portion coupling the arm portion to the elongated tubular component, wherein when the elbow portion is in a state of flexion, the arm portion is in a delivery configuration in which the elbow portion forms a distal end of the delivery catheter and in which the arm portion is substantially parallel with a longitudinal axis of the elongated tubular component. The arm portion is configured to carry a heart valve prosthesis. Accordingly, in some embodiments, the heart valve prosthesis delivery system can also include a heart valve prosthesis releasably attached to the arm portion.

In yet another aspect, embodiments of the present technology provide a delivery catheter for intravascular delivery of a heart valve prosthesis to a heart valve of a patient. The delivery catheter includes a delivery catheter comprising an elongated tubular component having a proximal segment and a distal segment, and an articulation assembly at the distal segment. The articulation assembly includes an arm portion coupled to the elongated tubular component by an elbow portion. In a state of flexion, the elbow portion positions the arm portion generally parallel to the elongated tubular component, e.g., for intravascular delivery of the distal segment of the delivery catheter to a target location. In a state of extension, the elbow portion positions the arm portion in a non-axial direction with respect to a longitudinal axis of the elongated tubular component, e.g., for orienting and positioning a heart valve prosthesis within the heart valve of the patient.

In a further aspect, embodiments of the present technology provide a method of delivering a mitral valve prosthesis to a native mitral valve of a patient. In one embodiment, the method can include intravascularly advancing an elongate tubular component of a delivery catheter from an aortic arch and across an aortic valve to a left ventricle of the patient, wherein the delivery catheter includes an articulation assembly in a delivery state at a distal end thereof. The articulation assembly has an arm portion carrying the mitral valve prosthesis and is coupled to the elongate tubular component by an elbow portion. The method may also include transitioning the elbow portion from a state of flexion to a state of extension to angle the arm portion away from a longitudinal axis of the elongate tubular component and toward the native mitral valve. The method may further include at least partially retracting the elongate tubular component of the delivery catheter to move the arm portion carrying the mitral valve device within the native mitral valve of the patient.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

DETAILED DESCRIPTION OF THE INVENTION

Specific embodiments of the present technology are now described with reference to the figures, wherein like reference numbers indicate identical or functionally similar elements. The terms "distal" and "proximal" are used in the following description with respect to a position or direction relative to the treating clinician or with respect to a catheter, catheter assembly, or delivery catheter. For example, "distal" or "distally" are a position distant from or in a direction away from the clinician when referring to delivery procedures or along a vasculature. Likewise, "proximal" and "proximally" are a position near or in a direction toward the clinician.

The following detailed description is merely exemplary in nature and is not intended to limit the present technology or the application and uses of the present technology. Although the description of embodiments hereof are in the context of treatment of heart valves and particularly in the context of gaining percutaneous access to a mitral valve, the present technology may also be used in any other body passageways where it is deemed useful. Furthermore, there is no intention to be bound by any expressed or implied theory presented in the preceding technical field, background, brief summary or the following detailed description.

Embodiments of the present technology as described herein can be combined in many ways to treat or access one or more of many valves of the body including valves of the heart such as the mitral valve. The embodiments of the present technology can be therapeutically combined with many known surgeries and procedures, for example, such embodiments can be combined with known methods of intravascularly accessing the valves of the heart such as the aortic valve and mitral valve with retrograde approaches and combinations of retrograde and antegrade approaches.

Figure 1:
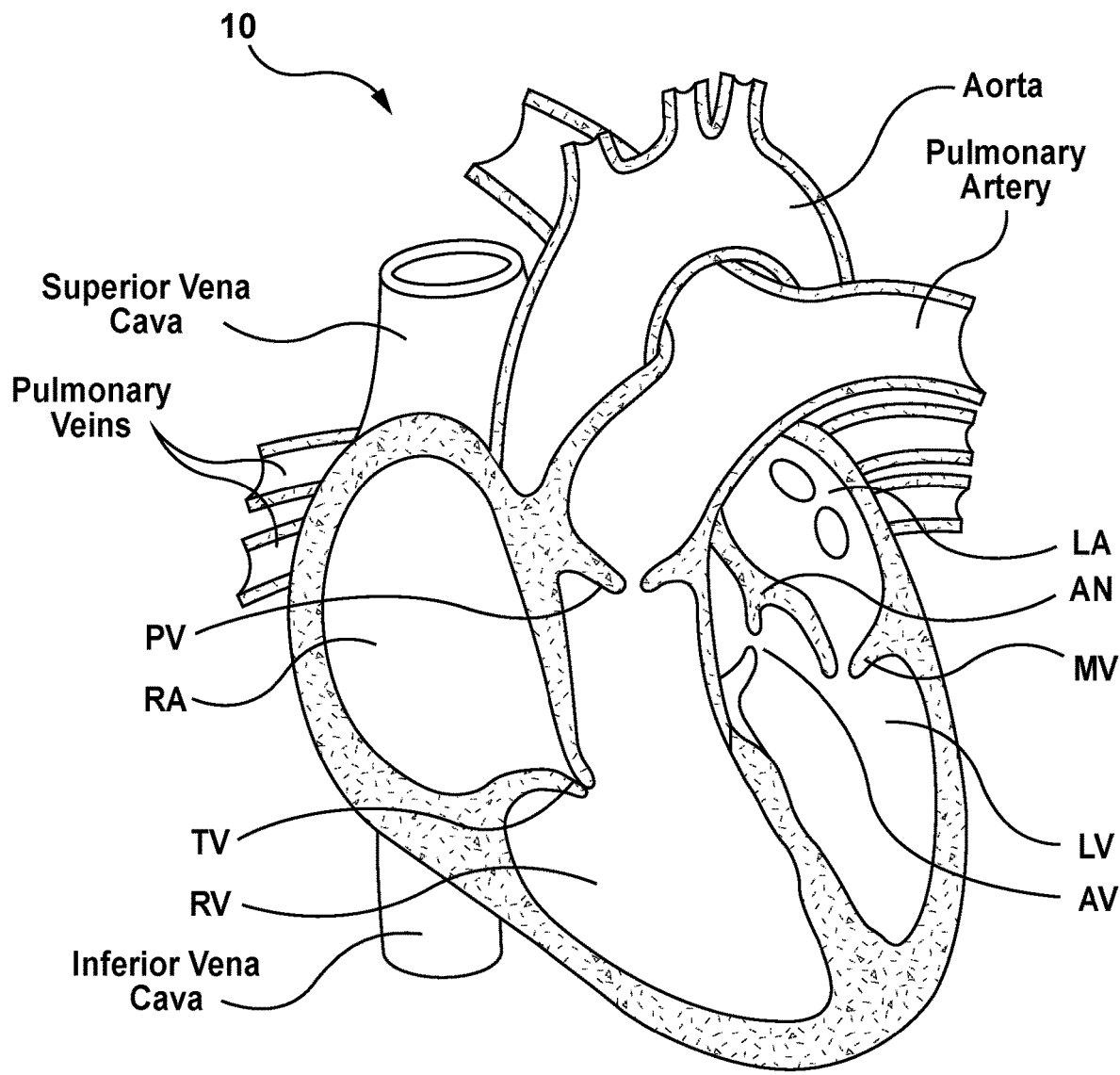
FIG. 1 is a schematic sectional illustration of a mammalian heart having native valve structures.
Figure 2A:
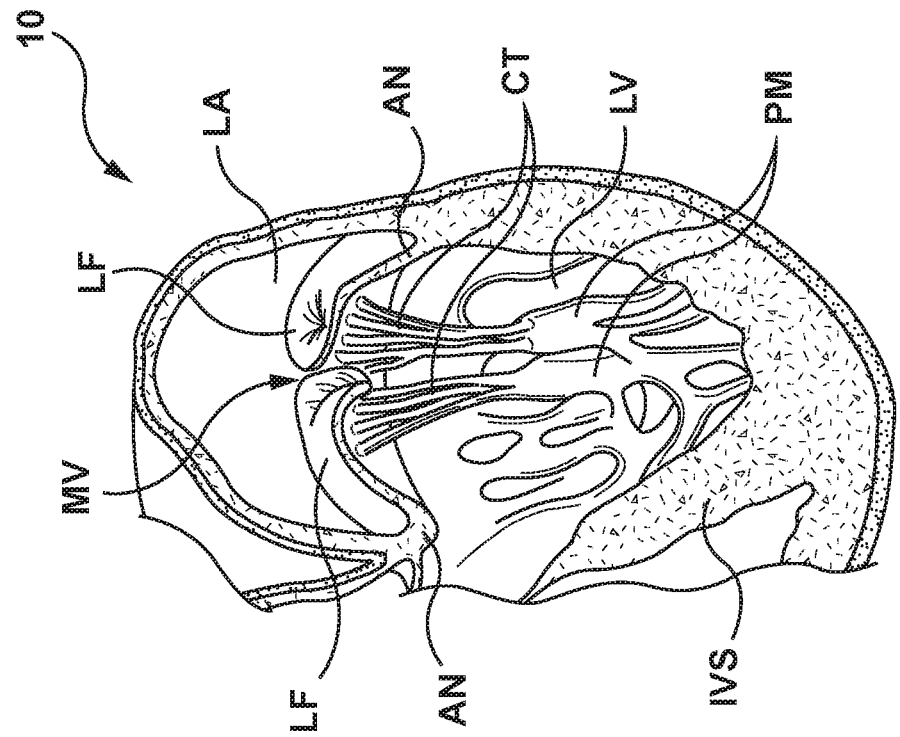
FIG. 2A is a schematic sectional illustration of a left ventricle of a mammalian heart showing anatomical structures and a native mitral valve.

FIG. 1 is a schematic sectional illustration of a mammalian heart 10 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2A is a schematic sectional illustration of a left ventricle LV of a mammalian heart 10 showing anatomical structures and a native mitral valve MV. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

Figure 2B:
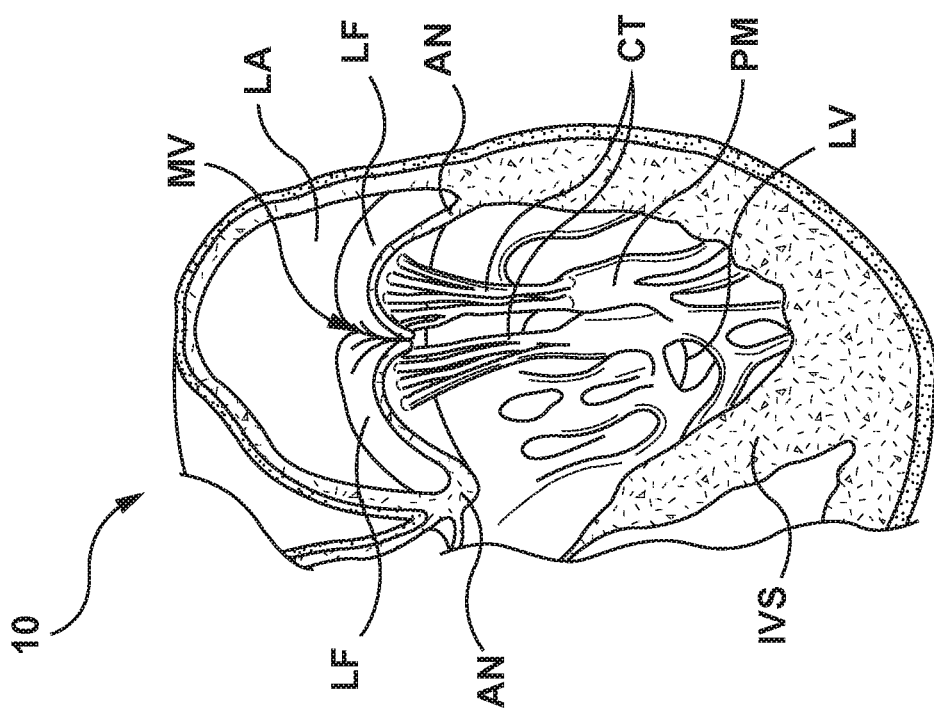
FIG. 2B is a schematic sectional illustration of the left ventricle of a heart having a prolapsed mitral valve in which the leaflets do not sufficiently co-apt and which is suitable for replacement with a prosthetic heart valve via a delivery system in accordance with embodiments hereof.

In a healthy heart, the leaflets LF of the mitral valve MV meet evenly at the free edges or "coapt" to close and prevent back flow of blood during contraction of the left ventricle LV (FIG. 2A). Referring to FIG. 2A, the leaflets LF attach the surrounding heart structure via a dense fibrous ring of connective tissue called an annulus AN which is distinct from both the leaflet tissue LF as well as the adjoining muscular tissue of the heart wall. In general, the connective tissue at the annulus AN is more fibrous, tougher and stronger than leaflet tissue. The flexible leaflet tissue of the mitral leaflets LF are connected to papillary muscles PM, which extend upwardly from the lower wall of the left ventricle LV and the interventricular septum IVS, via branching tendons called chordae tendinae CT. In a heart 10 having a prolapsed mitral valve MV in which the leaflets LF do not sufficiently coapt or meet, as shown in FIG. 2B, leakage from the left ventricle LV into the left atrium LA will occur. Several structural defects can cause the mitral leaflets LF to prolapse, and subsequent regurgitation to occur, including ruptured chordae tendinae CT, impairment of papillary muscles PM (e.g., due to ischemic heart disease), and enlargement of the heart and/or mitral valve annulus AN (e.g., cardiomyopathy).

Selected Embodiments of Delivery Systems and Methods for Prosthetic Valve Delivery Embodiments of delivery systems, delivery catheters, and associated methods in accordance with the present technology are described in this section with reference to FIGS. 3-12C. It will be appreciated that specific elements, sub-structures, uses, advantages, and/or other aspects of the embodiments described herein and with reference to FIGS. 3-12C can be suitably interchanged, substituted or otherwise configured with one another in accordance with additional embodiments of the present technology.

Provided herein are systems, assemblies, catheters, devices and methods suitable for intravascular delivery of a heart valve prosthesis to a native mitral valve in a heart of a patient. In some embodiments, delivery catheters and methods are presented for the treatment of valve disease as part of procedure steps for minimally invasive implantation of an artificial or prosthetic heart valve, such as a mitral valve. For example, a heart valve delivery system, in accordance with embodiments described herein, can be used to direct and deliver a mitral valve prosthesis via an intravascular retrograde approach across an aortic valve, into a left ventricle and across a diseased or damaged mitral valve in a patient, such as in a patient suffering from mitral valve prolapse illustrated in FIG. 2B. In another embodiment, a heart valve delivery system, in accordance with embodiments described herein, can be used to direct and deliver a mitral valve prosthesis via a venous transseptal approach across a right atria, through a transseptal wall, into a left atria and across a diseased or damaged mitral valve in a patient. In further embodiments, the delivery systems and delivery catheters disclosed herein are suitable for prosthetic heart valve delivery across other diseased or damaged natural heart valves or prior implanted prosthetic heart valves, such as tricuspid, pulmonary and aortic heart valves.

Figure 3:
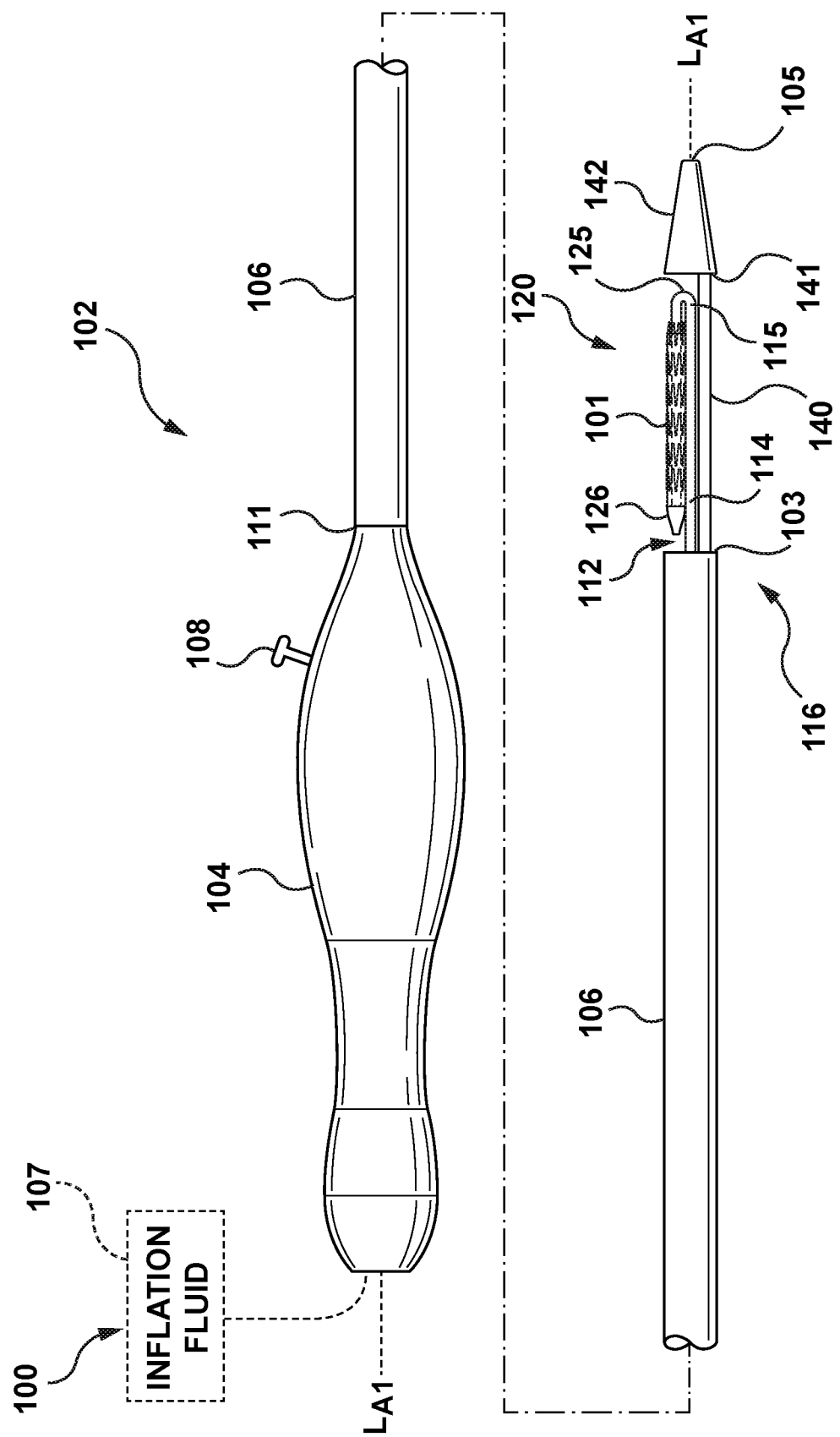
FIG. 3 is a side view of a minimally invasive heart valve prosthesis delivery system configured in accordance with an embodiment hereof.

FIG. 3 is a side view of a minimally invasive heart valve prosthesis delivery system 100 ("delivery system 100") configured in accordance with an embodiment hereof, wherein a compressed prosthetic valve device 101 is visible extending within a recessed segment or space 112 of a delivery catheter 102, between a distal end 103 of an elongate outer tubular component 106 and a distal tip 142 of the delivery catheter 102. In an embodiment, a self-expanding prosthetic valve device 101 is held in its compressed, delivery state by a cinch device or one or more loops of a suture/sutures (not shown), as described below. The delivery system 100 may be used to align and deliver the prosthetic valve device 101 to a target region of the heart for repair or replacement of a diseased or damaged heart valve of a patient. In some instances, the delivery system 100 may be used to deliver and align the prosthetic valve device 101 by a retrograde approach to the mitral valve that includes an intravascular path from the aortic arch, across the aortic valve, and into the left ventricle of a patient, and beneficially the delivery catheter 102 thereof does not include a capsule or other prosthesis covering component over the compressed prosthetic valve device 101 and thereby has improved flexibility and a reduced delivery profile, particularly in a distal segment 116 thereof. As well, the delivery catheter 102 without a capsule or other prosthesis covering component over the compressed prosthetic valve device 101 eliminates the need to retract or advance a capsule or other prosthesis covering component relative to the prosthetic valve device during delivery, and therefore can be more efficiently utilized within the confines of the left ventricle in a retrograde approach. In embodiments hereof, an introducer sheath (not shown) or an outer sheath (not shown) may be used with the delivery catheter 102 to minimize intravascular trauma during introduction, tracking and delivery of the delivery catheter 102 to a target location.

As shown in FIG. 3, the delivery system 100 includes the delivery catheter 102 having a handle component 104 operatively coupled to a remainder thereof as described herein. A first tubular component or elongated shaft 114 of the delivery catheter 102 is slidable or translatable relative to the outer tubular component 106. Further, the first tubular component 114 is configured to extend from at least a distal end 111 of the handle component 104 to a distal segment 116 of the delivery catheter 102, as described in more detail below. The delivery system 100 is sized and configured to be advanced through the vasculature in a minimally invasive manner. In embodiments incorporating hydraulic expanding components and/or for delivering/deploying a balloon-expandable prosthetic heart valve device, the delivery system 100 includes an inflation fluid source 107, as shown in FIG. 3, operatively coupled to the handle component 104 or other portion of the delivery catheter 102, to facilitate communication between a hydraulic expanding component and/or a balloon assembly (not shown) and the source of inflation fluid 107.

The delivery catheter 102 further includes an articulation assembly 120 disposed within the distal segment 116 thereof, and extended from a distal end 115 of the first tubular component 114. The articulation assembly 120 is configured for orienting and positioning the prosthetic valve device 101 within or adjacent to a native heart valve (e.g., mitral valve) and for deployment of the valve device 101. In an embodiment, the first tubular component 114 can have a generally hollow body that extends between the handle component 104 and the articulation assembly 120.

Figure 4A:
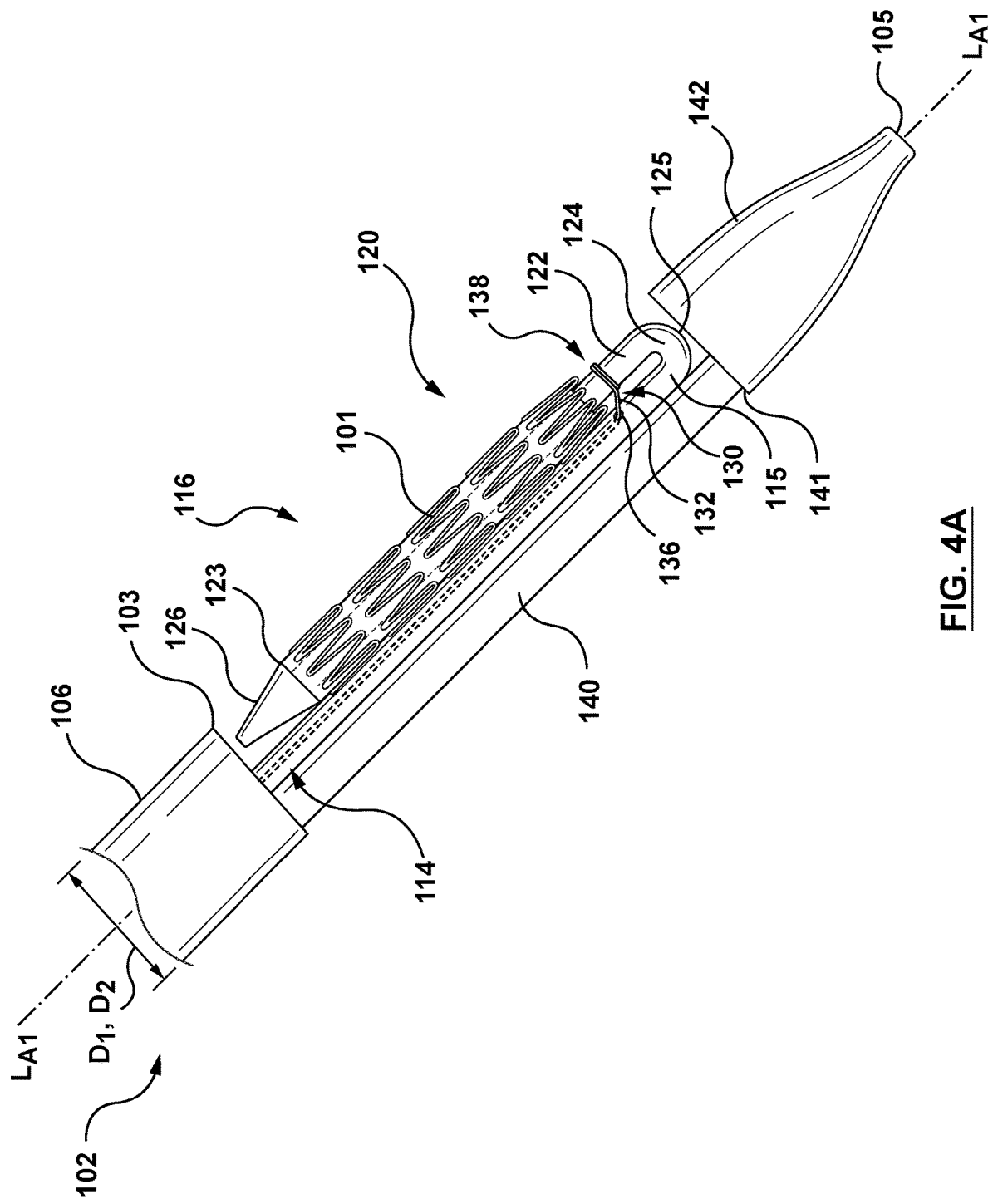
FIG. 4A is a partial side view of a distal segment of a delivery catheter for use with the heart valve prosthesis delivery system of FIG. 3 shown in a delivery configuration in accordance with an embodiment hereof.
Figure 4B:
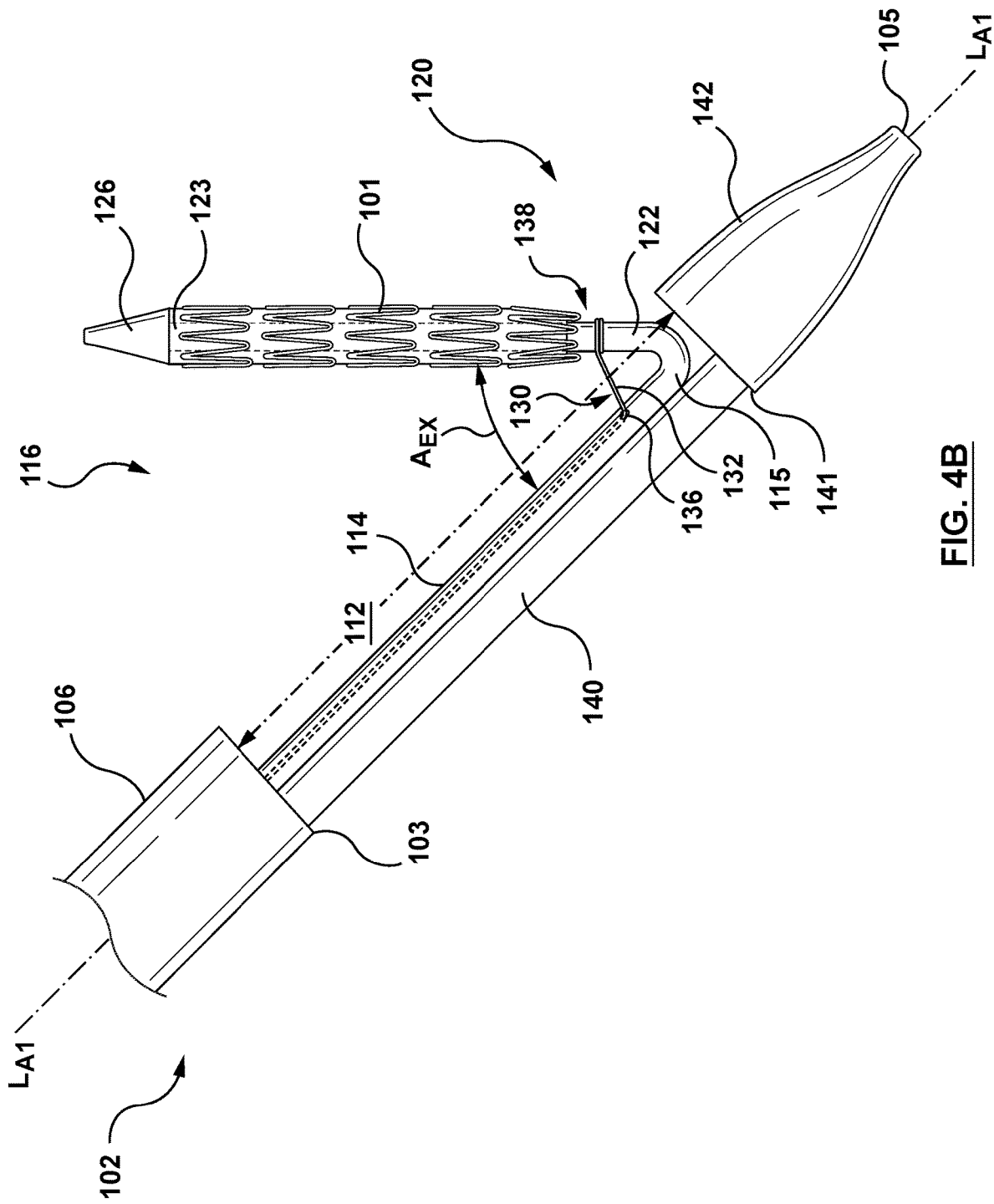
FIG. 4B is a partial side view of the delivery catheter of FIG. 4A in a deployed configuration in accordance with an embodiment hereof.

FIG. 4A is an enlarged partial side view of the distal segment 116 of the delivery catheter 102 in a delivery configuration with the articulation assembly 120 having a low profile or closed state in accordance with an embodiment hereof. FIG. 4B is an enlarged partial side view of the delivery catheter 102 of FIG. 4A in a deployed configuration with the articulation assembly 120 having an outwardly angled or open state in accordance with an embodiment hereof. Referring to FIGS. 3-4B together, the articulation assembly 120 includes an arm portion 122 coupled to, or extending from, the distal end 115 of the first tubular component 114 by an elbow or hinge portion 124. The elbow portion 124 forms a distal end 125 of the articulation assembly 120 when the delivery catheter 102 is in the delivery configuration as shown in FIGS. 3 and 4A. The distal segment 116 of the delivery catheter 102 can be configured to be delivered intravascularly to a target location (e.g., target heart chamber) of a human patient in the delivery configuration with the articulation assembly 120 having the low-profile, substantially straightened or closed state shown in FIG. 4A. Upon delivery to a target location, when the delivery catheter 102 is in the deployed configuration of FIG. 4B, the articulation assembly 120, in accordance with embodiments hereof, is further configured to be transformed into the outwardly angled or opened state in which the arm portion 122 is angled away from the first tubular component 114 via an outward opening or extension of the elbow portion 124.

Referring to FIG. 4A, when the delivery catheter 101 is in the delivery configuration, the arm portion 122 is positioned generally parallel with a longitudinal axis $L_{A1}$ of the first tubular component 114, and is configured to carry the prosthetic valve device 101 in a low-profile or closed state for delivery through the vasculature. Accordingly, the articulation assembly 120 is configurable into the low-profile or closed configuration in which the elbow portion 124 is in a state of flexion and wherein an angle (not shown) formed between the arm portion 122 and the first tubular component 114 is substantially 0 degrees (FIG. 4A). Stated another way, when the articulation assembly 120 is in the low-profile or closed configuration, the elbow portion is closed such that the arm portion 122 and the first tubular component 114 are substantially parallel (FIG. 4A). Referring to FIGS. 4A and 4B together, an outward opening of the elbow portion 124, in which the elbow portion 124 may be referred to as being in a state of extension relative to the first tubular component 114, permits the arm portion 122 to angle away from the longitudinal axis $L_{A1}$ of the first tubular component 114 thereby transitioning the delivery catheter 102 to the deployed configuration (FIG. 4B).

In the delivery configuration, the delivery catheter 102 is configured to be introduced within a patient's vasculature to position the prosthetic heart valve 101 at a target location such as a heart chamber (e.g., left ventricle) adjacent a damaged or diseased heart valve (e.g., mitral valve). Upon advancement/delivery to the target location (e.g., left ventricle), the delivery catheter 102 is transformable to a deployed configuration (FIG. 4B) with the articulation assembly 120 having an outwardly angled or open state (e.g., the arm portion 122 is angled away from the longitudinal axis $L_{A1}$ of the first tubular component 114) for aligning and positioning the prosthetic valve device 101 within the damaged or diseased heart valve for repair or valve replacement. Referring to FIG. 4B, an extension angle $A_{EX}$ formed between the arm portion 122 and the first tubular component 114 is greater than 0 degrees. For example, the extension angle $A_{EX}$ can be between about 30° and about 90°, between about 40° and about 90°, between about 45° and about 90°, or less than about 90°. In other embodiments, the extension angle $A_{EX}$ can be greater than about 90°. In the deployed/open state, as shown in FIG. 4B, the articulation assembly 120 of the delivery catheter 102 positions the prosthetic valve device 101 in a non-parallel orientation with respect to the first tubular component 114 and, in some embodiments, can be further adjusted (e.g., the adjustment of the extension angle $A_{EX}$) to selectively align the prosthetic valve device 101 with a native valve region such as, for example, within or adjacent a native valve annulus or a region of leaflet coaptation of the damaged or diseased heart valve.

Figure 4C:
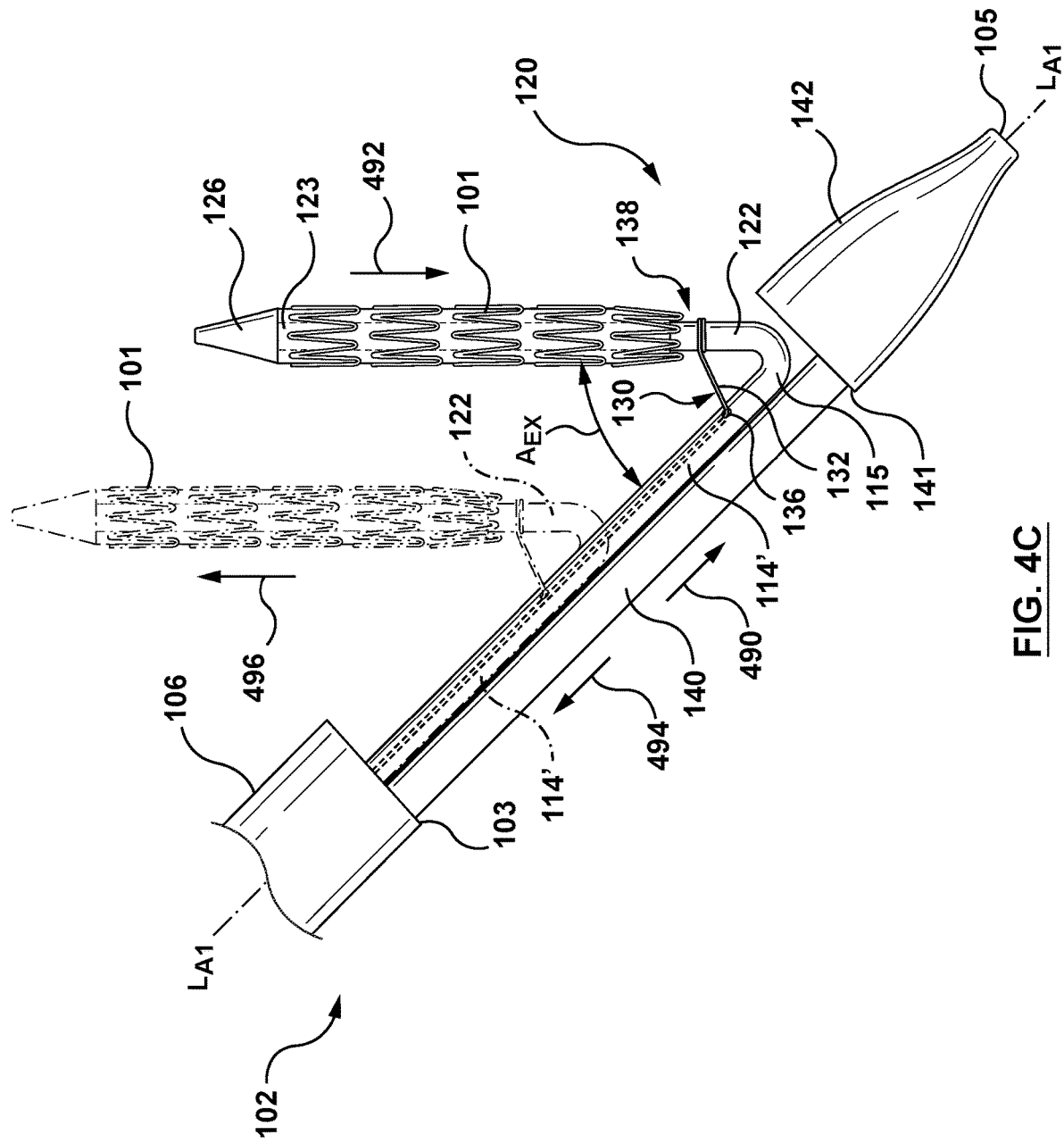
FIG. 4C is a partial side view of a delivery catheter, which is similar to the one shown in FIG. 4A, in a deployed configuration in accordance with another embodiment hereof.

In another embodiment shown in FIG. 4C, the delivery catheter 102 is modified to include a first tubular component 114' that is longitudinally slidable or translatable relative to the second tubular component 140. First tubular component 114' is translatable via remote actuation, e.g., via an actuator such as a knob, pin, or lever, of the handle component 104. In the deployed/open state, the valve device 101 can be selectively aligned with the native mitral valve via longitudinal translational adjustment of the first tubular component 114' within the recessed segment 112. Stated another way, a clinician can slidably advance the first tubular component 114' in a distal direction (e.g., in the direction of arrow 490) to move the arm portion 122 in the deployed state in the distal direction and, likewise, a clinician can retract the first tubular component 114' in a proximal direction (e.g. in the direction of arrow 494) to move the arm portion 122 in the deployed state in the proximal direction to thereby adjust the alignment of the valve device 101 with the native mitral valve for subsequent deployment therein.

The arm portion 122 may be transitioned between the closed (delivery) state and the open (deployed) state (that correspond to the delivery and deployed configurations of the delivery catheter 102) using a variety of suitable mechanisms or techniques (e.g., shape memory, mechanical actuation of the elbow portion 124 using push/pull wires, and/or using a hydraulic mechanism). In an embodiment, the articulation assembly 120 may be integral with the distal end 115 of the first tubular component 114 and together have a tubular structure with a shape memory to transform into the open (deployed) state when unrestricted or untensioned. In another embodiment, the articulation assembly 120 may be a separate, tubular structure having a shape memory, to return to an open (deployed) state), that is coupled to the first tubular component 114. For example, in one embodiment, at least a portion of the articulation assembly 120 has been shape-set to provide the elbow portion 124 with a curved shape, that when unrestrained, orients the arm portion 122 in a non-parallel direction, or at an angle, with respect to the longitudinal axis $L_{A1}$ of the first tubular structure 114. In another embodiment, a tubular structure may be shape-set such that the first tubular component 114, the elbow portion 124 and the arm portion 122 are generally straight (e.g., are in axial alignment with the longitudinal axis $L_{A1}$), and wherein the elbow portion 124 has a lower stiffness than each of the arm portion 122 and the first tubular component 114 such that the elbow portion 124 may be preferentially bent when the arm portion 122 is restrained against the first tubular component 114. The arm portion 122 may then be actuated or restrained by various methods such as, but not limited to a tether line 132, described in greater detail below.

Referring to the embodiment shown in FIGS. 4A and 4B, extension of the elbow portion 124 may be permitted by loosening or slackening a tether device 130 attached to the arm portion 122 and deployable via remote actuation, e.g., via an actuator 108 (FIG. 3), such as a knob, pin, or lever carried by the handle component 104. Referring to FIGS. 3-4B together, the tether device 130 includes the tether line 132 (such as elongated cord, wire or a suture) that extends from the handle component 104 (or other proximal position of the delivery catheter 102 that is controllable from outside of the body), through a hole 136 or recess formed in a distal portion of the first tubular component 114, and to an attachment point 138 on the arm portion 122. As shown in FIGS. 4A and 4B, the tether line 132 is secured (such as by a loop) to the arm portion 122 at the attachment point 138. When transitioning the articulation assembly 120 from the closed (delivery) state to the open (deployed) state, the tether line 132 can be relaxed or slackened via the actuator 108, allowing the shape-set elbow portion 124 to resume or return to its shape memory state and thereby causing the arm portion 122 to be angled away from the first tubular component 114 (e.g., in a non-parallel direction with respect to the longitudinal axis $L_{A1}$). Once deployed, adjustment of the extension angle $A_{EX}$ is possible by tightening (e.g., retracting) or relaxing/slackening (e.g., advancing) the tether line 132 until a desired extension angle $A_{EX}$ is achieved that orients or aligns the prosthetic valve device 101 for deployment in a target native valve. Likewise, the articulation assembly 120 transitions from the open (deployed) state to the closed (delivery) state when the tether line 132 is retracted, causing flexion of the elbow portion 124 until the arm portion 122 is generally parallel with the longitudinal axis $L_{A1}$ (e.g., the extension angle $A_{EX}$ is substantially 0 degrees).

Referring to FIGS. 4A and 4B, the articulation assembly 120 and/or the first tubular component 114 can be a tubular structure having a shape memory property comprising a nickel titanium alloy (e.g., nitinol) multi-filar stranded wire with a lumen therethrough, such as, for example, as sold under the trademark HELICAL HOLLOW STRAND (HHS), and commercially available from Fort Wayne Metals of Fort Wayne, Ind. In another embodiment, the articulation assembly 120 and/or the first tubular component 114 can be a nitinol tube with a laser cut pattern in an elbow portion (e.g. interrupted spiral) that permits articulation thereof. The articulation assembly and/or portions thereof (e.g., the arm portion 122, the elbow portion 124) may be formed from a variety of different types of materials, may be arranged in a single or dual-layer configuration, and may be manufactured with a selected tension, compression, torque, pitch direction, or other characteristics. The HHS material, for example, may be cut using a laser, electrical discharge machining (EDM), electrochemical grinding (ECG), or other suitable means to achieve a desired finished component length and geometry.

Forming the articulation assembly 120 of nitinol multi-filar stranded wire(s) or other similar materials is expected to provide a desired level of support and rigidity to the articulation assembly 120 without additional reinforcement wire(s) or other reinforcement features within the articulation assembly 120, thereby providing support to the prosthetic valve device 101 during delivery and implantation. In one embodiment, the curved shape structure of the elbow portion 124 can be formed from a shape memory material (e.g., nitinol) wire or tube that is shaped around a mandrel (not shown) using conventional shape-setting techniques known in the art. A desired stiffness of the articulation assembly 120 and/or variable stiffness of the arm and elbow portions 122, 124 can be provided using variations in a braid or weave pattern, coiled structures, woven structures and/or wire density. For example, the stiffness of the first tubular component 114 and/or the articulation assembly 120 shown in FIGS. 4A and 4B can vary along a length of the first tubular component 114, the arm and elbow portions 122, 124 and/or in transition regions therebetween. In an embodiment hereof, as described above, for example, regions at or near the arm portion 122 and the first tubular component 114 may have a greater stiffness than regions comprising the elbow portion 124.

In other embodiments, the first tubular component 114 and/or other components of the articulation assembly 120 may be composed of different materials and/or have a different arrangement. For example, the elbow portion 124 may be formed from other suitable shape memory materials (e.g., wire or tubing besides HHS or nitinol, shape memory polymers, electro-active polymers) that are pre-formed or pre-shaped into the desired deployed state. Alternatively, the first tubular component 114 and/or other components of the articulation assembly 120 may be formed from multiple materials such as a composite of one or more polymers and metals. In still other embodiments, and as discussed in greater detail below, the articulation assembly 120 may not be self-expanding and is transformed between the delivery and deployed states using other suitable mechanisms or techniques (e.g., actuation of a push wire, actuation via fluid pressure and/or partial inflation, etc.).

Referring to FIGS. 3-4B together, the articulation assembly 120 terminates with a first atraumatic tip 126 to facilitate introduction and movement of the arm portion 122 within the target heart chamber and towards the target valve region (e.g., when in the open (deployed) state) in a manner that prevents or reduces trauma to the surrounding heart tissue structures (e.g., chordae tendinae, papillary muscles, leaflets, annulus, etc.). The first atraumatic tip 126 can be a flexible curved or tapered tip. The curvature of the first atraumatic tip 126 can be varied depending upon the particular sizing/configuration of the articulation assembly 120 and/or the prosthetic valve device 101. In some embodiments, the first atraumatic tip 126 may also comprise one or more radiopaque markers (not shown) and/or one or more sensors (not shown) for facilitating positioning and placement of the articulation assembly 120 and/or the prosthetic valve device 101 by the clinician or operator. In one embodiment, the first atraumatic tip 126 can be part of the articulation assembly 120 (e.g., an extension of or integral with the arm portion 122). In one example, the first atraumatic tip 126 can be a more flexible tapered portion (e.g., about 5 to about 7 mm) of a terminal end of the arm portion 122. In another embodiment, the first atraumatic tip 126 can be a separate component that may be affixed to a terminal end 123 of the arm portion 122 and/or articulation assembly 120 via adhesive, crimping, over-molding, or other suitable techniques. The first atraumatic tip 126 can be made from a polymer material (e.g., a polyether block amide copolymer sold under the trademark PEBAX, or a thermoplastic polyether urethane material sold under the trademarks ELASTHANE or PELLETHANE), or other suitable materials having the desired properties, including a selected durometer. In other embodiments, the first atraumatic tip 126 may be formed from different material(s) and/or have a different arrangement. In other embodiments, the first atraumatic tip 126 may be steerable, i.e., include a steering mechanism, in order to aid in the alignment and adjustment of a position of the valve device 101 within the native valve region. In an embodiment, the steering mechanism may include a pull-wire, such as a pull-wire 190 discussed below, coupled to the first atraumatic tip 126 that it is actuatable to steer the tip.

Referring to back to FIG. 3, the delivery catheter 102 also includes a second tubular component or elongated shaft 140 extending parallel with the first tubular component 114 from the handle component 104 to the distal segment 116 of the delivery catheter 102. The second tubular component 140 can also have a generally hollow body that extends between the handle component 104 and the distal segment 116 and which can define therethrough a lumen (not shown) configured to slidably receive a guidewire (not shown). As would be understood by one of skill in the art, the delivery catheter 102 having the articulation assembly 120 may be tracked over an indwelling guidewire to a target location adjacent a damaged or diseased heart valve when in the delivery configuration of FIGS. 3 and 4A. The first and second tubular components 114, 140 may be formed from the same or similar types of materials and include similar manufacturing features that impart a selected tension, compression, torque, pitch direction, and/or other characteristics. In certain embodiments, the second tubular component 140 provides an elongated shaft configured to receive a guidewire in a lumen (not shown) provided therethrough. In other embodiments, the second tubular component 140 may be steerable itself such that the distal segment 116 of the delivery catheter 102 may be tracked to the treatment site without the aid of a guidewire (not shown).

As shown in FIGS. 3-4B, the delivery catheter 102 can further include a second atraumatic tip or distal tip 142, coupled to a distal end 141 of the second tubular component 140. The second atraumatic tip 142 provides a flexible curved or tapered tip to the delivery catheter 102 to permit it to be advanced through the vasculature without causing intravascular trauma during introduction, tracking and delivery of the delivery catheter, and specifically the prosthetic valve device 101, to a target location. The second atraumatic tip 142 is a separate component that may be affixed to the distal end 141 of the second tubular component 140 via adhesive, crimping, over-molding, or other suitable techniques. As illustrated in FIG. 4A, the second atraumatic tip 142 has a cross-sectional dimension or outer diameter $D_1$ generally similar to and aligned with a cross-sectional dimension or outer diameter $D_2$ of the outer tubular component 106, and is spaced from the distal end 103 of the outer tubular component 106 such that a recessed segment 112 of the delivery catheter 102 is defined there between. The second atraumatic tip 142 can be made from similar materials as those described above for the first atraumatic tip 126.

In one embodiment, the second atraumatic tip 142 can include a passage (not shown) aligned with the lumen of the second tubular component 140 for facilitating an over-the-wire ("OTW") delivery of the delivery catheter 102 to a target location. For example, the second atraumatic tip 142 may define a distal opening or port 105 for receiving a guidewire for delivery of the delivery catheter 102 using OTW techniques. In other embodiments, a delivery catheter in accordance herewith may be adapted to have a guidewire lumen along only a distal segment thereof so as to be suitable for use with rapid-exchange ("RX") techniques. In additional embodiments, the first and/or second atraumatic tips 126, 142 or other features associated with the first and/or second tubular components 114, 140 and/or articulation assembly 120 (e.g., arm portion 122, elbow portion 124) can include radiopaque markers and/or be formed of radiopaque materials (e.g., barium sulfate, bismuth trioxide, bismuth subcarbonate, powdered tungsten, powdered tantalum, or various formulations of certain metals, including gold and platinum) that are capable of being fluoroscopically imaged to allow a clinician to determine if the articulation assembly 120 is appropriately placed and/or deployed within or adjacent the target heart valve (e.g., mitral valve).

In operation, the delivery catheter 102 can be configured to allow locational adjustment of the orientation and placement of the prosthetic valve device 101 for repair or replacement of a diseased or damaged native valve or prior implanted prosthetic valve in a patient, such as in a patient suffering from mitral valve prolapse illustrated in FIG. 2B. For example, the articulation assembly 120 can be adjusted via extension and flexion of the elbow portion 124, as discussed above, allowing fine control over the orientation and placement of the prosthetic valve device 101 with respect to the target native valve structure. Further, the articulation assembly 120 can stably position a prosthetic valve device 101 within a native mitral valve using a retrograde approach (e.g., through the aortic valve into the left ventricle) in an atraumatic manner (e.g., without unintentional damage to the aortic valve, left ventricle or native mitral valve tissue). Accordingly, the catheters and methods described can also provide a clinician or operator with improved control and placement of the prosthetic valve device 101 for implantation at the native mitral valve during delivery across the aortic valve using a retrograde approach.

Figure 5A:
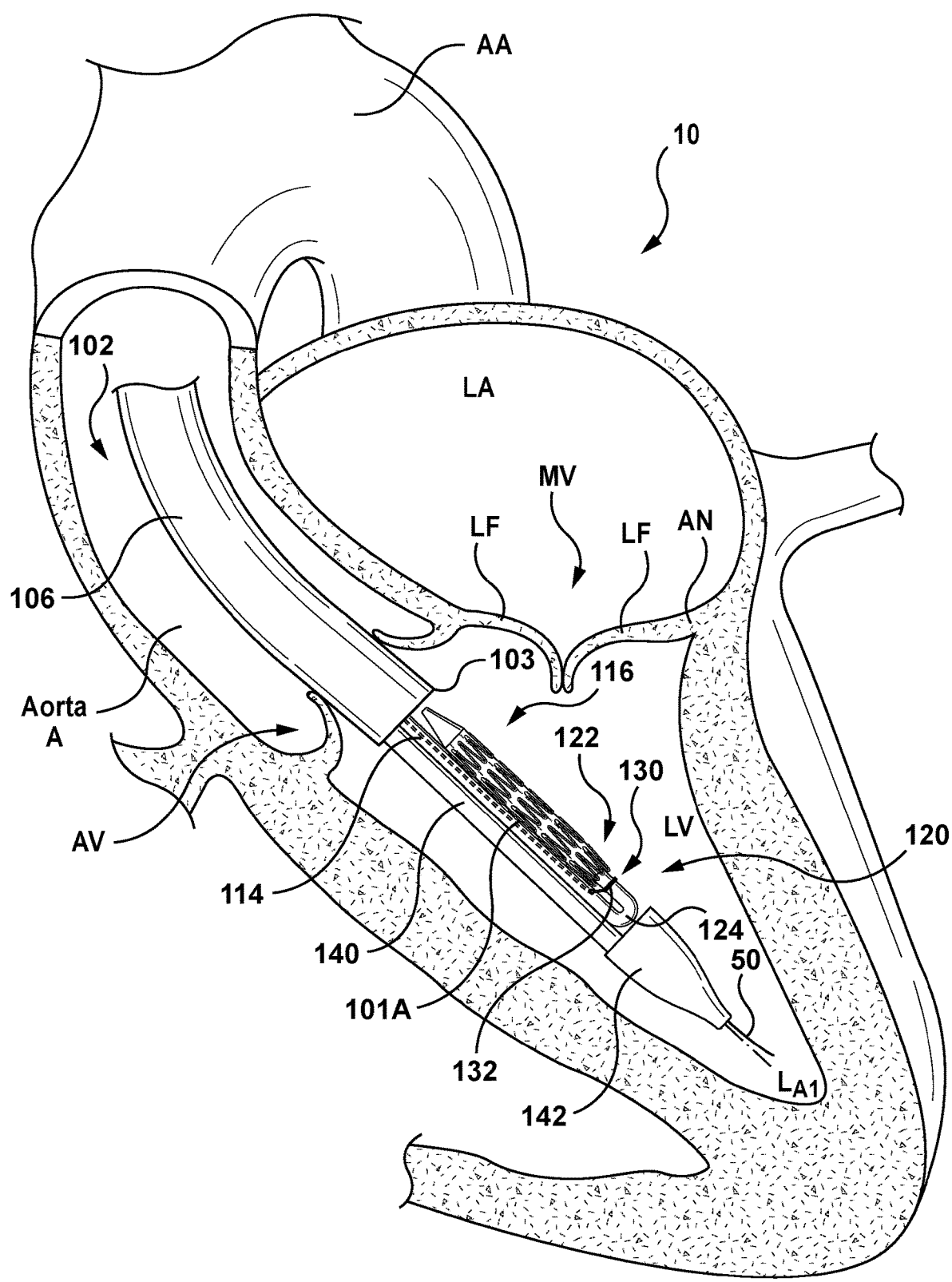
FIGS. 5A-5C are sectional cut-away views of the heart illustrating a method of delivering and positioning a mitral valve prosthesis using a retrograde approach in accordance with an embodiment hereof
Figure 5B:
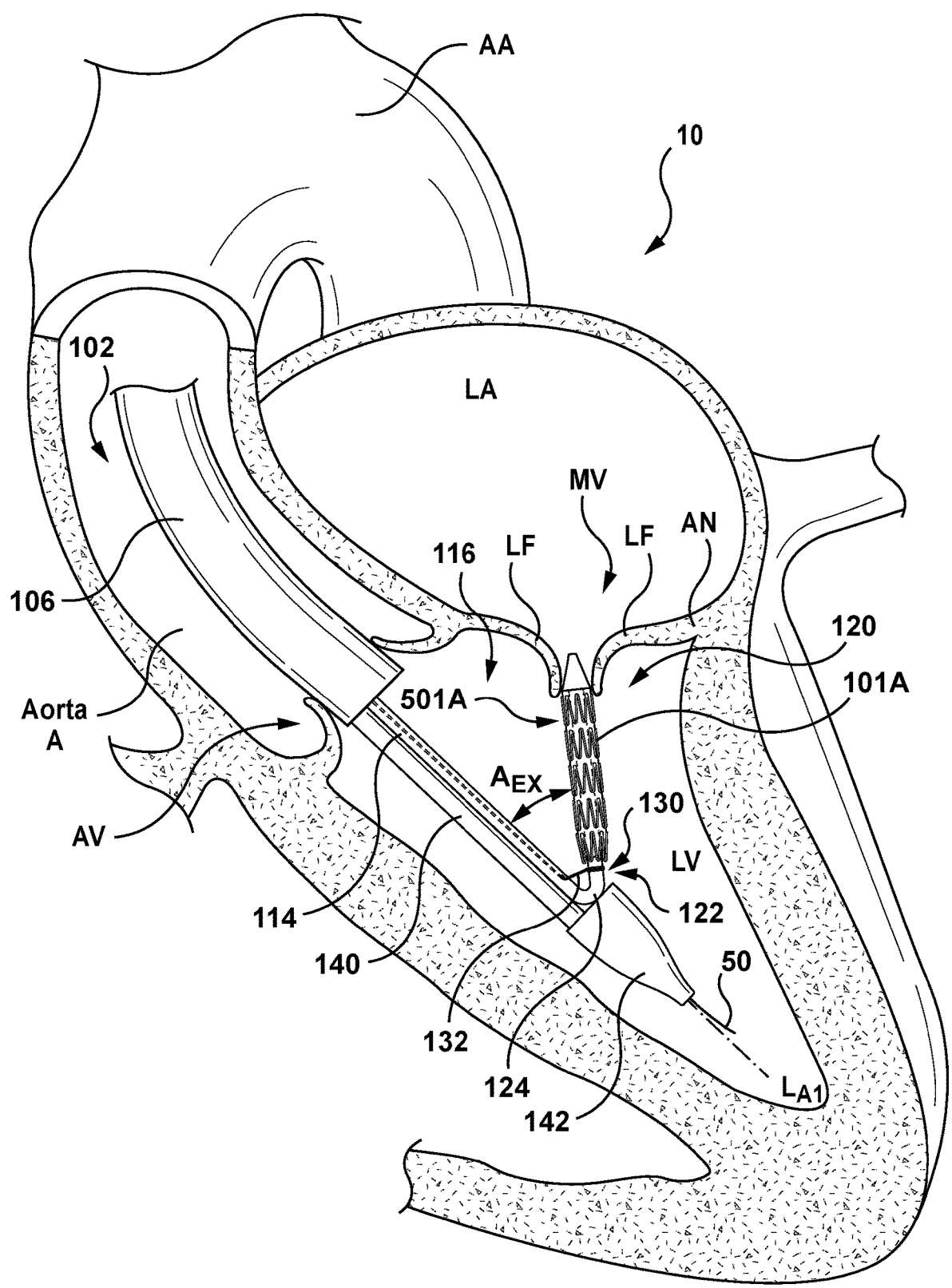
Figure 5C:
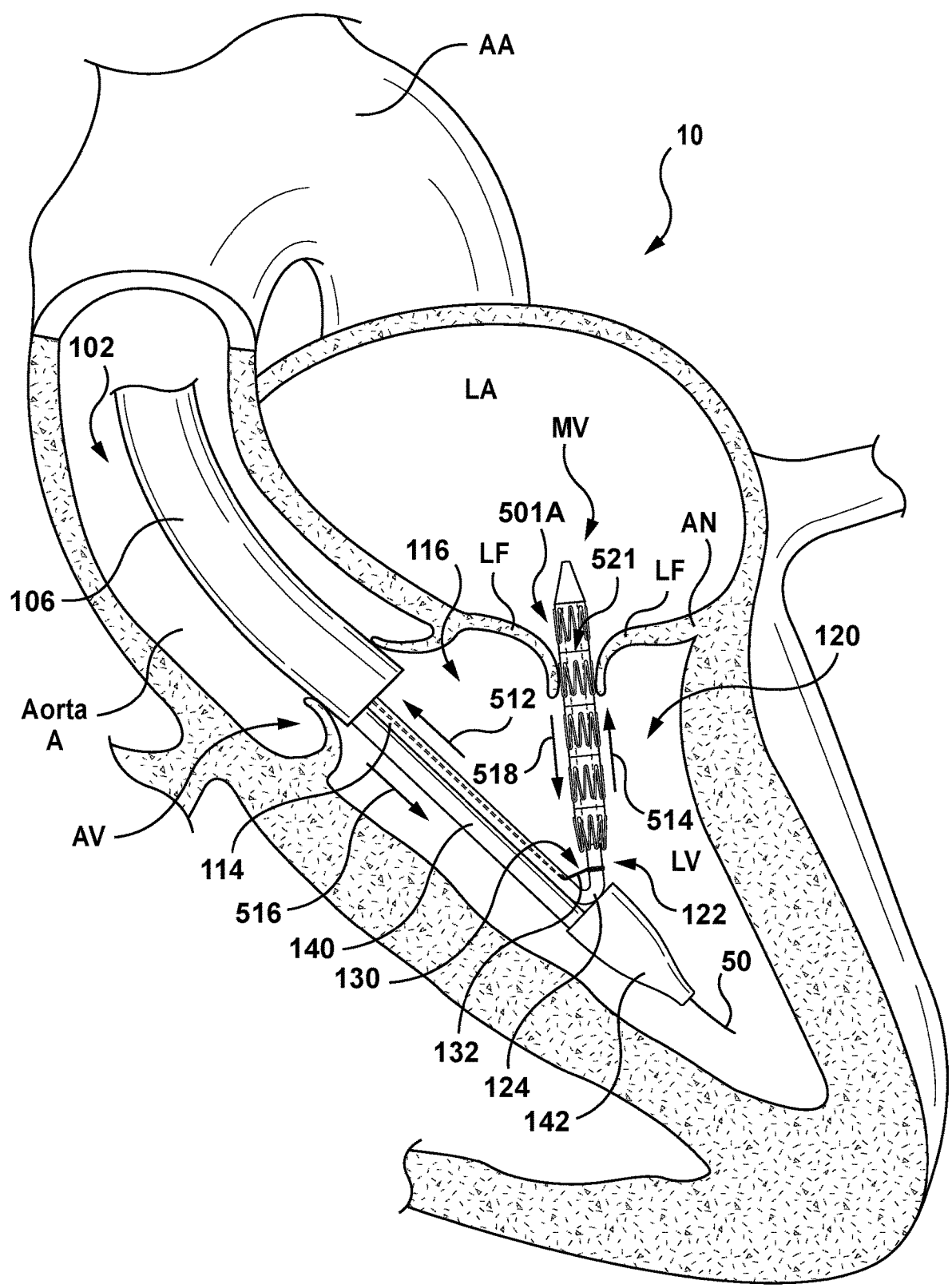

FIGS. 5A-5C are sectional cut-away views of the heart 10 illustrating a retrograde approach for delivering and positioning a mitral valve prosthesis 101A using the delivery system 100 of FIGS. 3-4B and in accordance with an embodiment hereof. Referring to FIGS. 5A-5C together, the distal segment 116 of the delivery catheter 102 having the articulation assembly 120 is shown positioned in the left ventricle LV, and the outer tubular component 106 housing the first and second tubular components 114, 140 of the delivery catheter 102 is shown in an intravascular path extending from the aortic arch AA, through the ascending aorta A, and crossing the aortic valve AV. Intravascular access to the aortic arch AA and ascending aorta A can be achieved via a percutaneous access site in a femoral, brachial, radial, or axillary artery. Referring back to FIG. 3, and as is known in the art, the handle component 104, as well as some length of a proximal segment of the delivery catheter 102, are exposed externally of the patient for access by a clinician, even as the articulation assembly 120 carrying the mitral valve prosthesis 101A has been advanced fully to the targeted site (e.g., left ventricle LV) in the patient. By manipulating the handle component 104 (FIG. 3) of the delivery catheter 102 from outside the vasculature, a clinician may advance and remotely manipulate and steer the distal segment 116 of the delivery catheter 102 through the sometimes tortuous intravascular path.

Referring back to FIGS. 5A-5C, the articulation assembly 120 of the delivery catheter 102 may be advanced into the left ventricle LV and positioned generally below (e.g., downstream) of the mitral valve MV. Optionally, and as shown in FIG. 5A, a guidewire 50 may be used over which the delivery catheter 102 (e.g., via the second tubular component 140 and second atraumatic tip 142) may be slidably advanced. In a next delivery step shown in FIG. 5B, the articulation assembly 120 is transitioned from the closed (delivery) state to the open (deployed) state in which the arm portion 122 is angled away from the longitudinal axis $L_{A1}$ of the first tubular component 114. As described above, actuation of the tether device 130 provides slack in the tether line 132 thereby allowing extension of the elbow portion 124 (e.g., to bias toward or return to a pre-shaped or shape set configuration). As illustrated, the extension angle $A_{EX}$ is less than 90° when orienting the mitral valve prosthesis 101A with respect to the native mitral valve MV. In this phase of delivery, the mitral valve prosthesis 101A is positioned within the left ventricle LV and generally below (e.g., downstream) of the native mitral valve MV. In a next delivery step shown in FIG. 5C, the delivery catheter 102 is partially retracted along the intravascular path to bring the arm portion 122 carrying the mitral valve prosthesis 101A into proximity to and/or apposition with the mitral valve annulus AN and/or leaflets LF. For example, movement of the delivery catheter 102 in the proximal direction (along arrow 512) translates to movement of the arm portion 122 in the direction of arrow 514 toward the mitral valve anatomy.

Figure 5D:
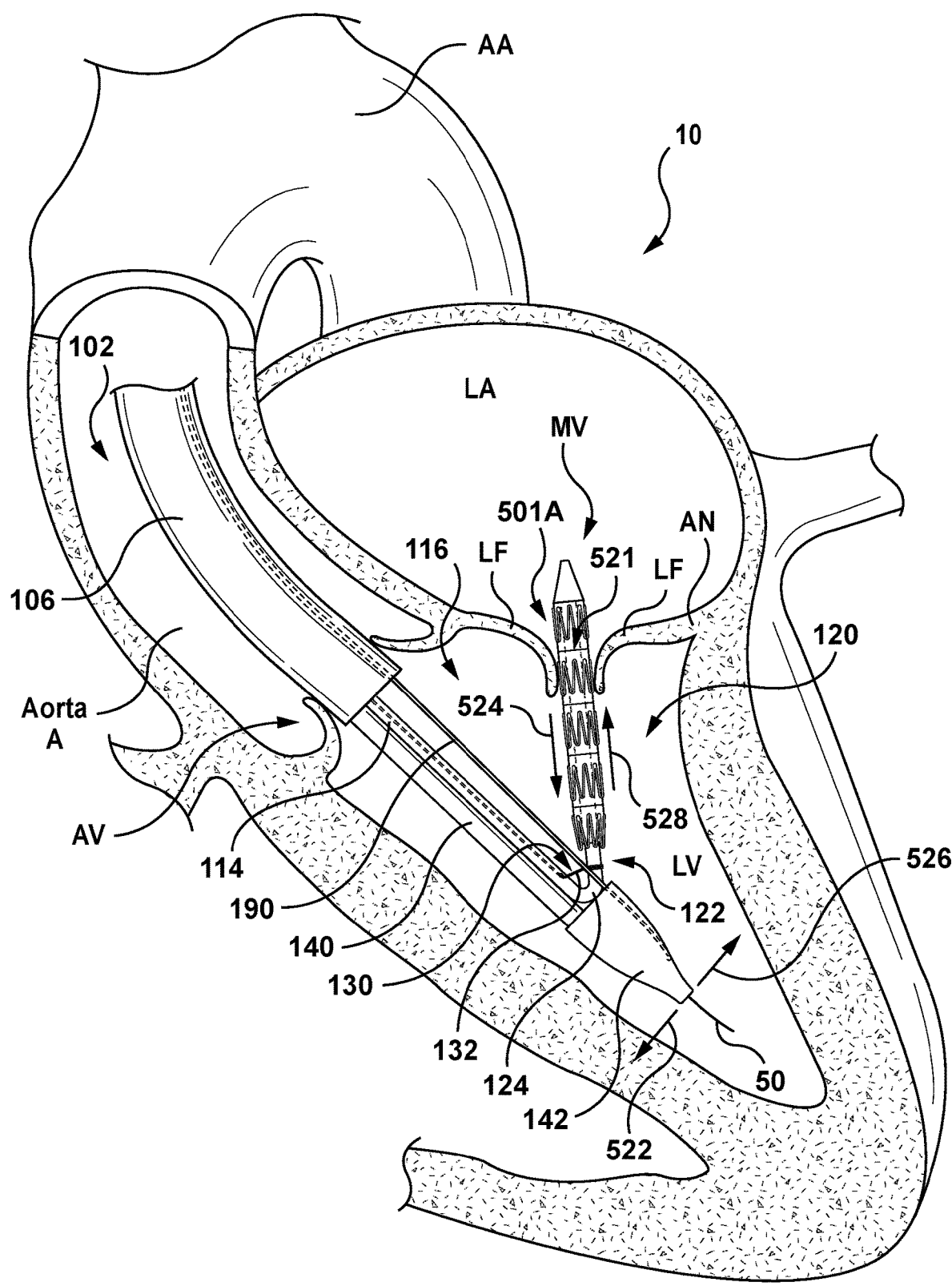
FIG. 5D is a sectional cut-away view of the heart illustrating a method of delivering and positioning a mitral valve prosthesis using a retrograde approach in accordance with another embodiment hereof

In another embodiment shown in FIG. 5D, the second atraumatic tip 142 can include a steering mechanism configured to manipulate/steer the distal segment 116 of the delivery catheter 102. The steering mechanism may include a pull-wire 190 coupled to the second atraumatic tip 142. The pull-wire 190 may extend within the outer tubular component 106 and to the handle component 104 (FIG. 3) where it is actuatable via remote actuation, e.g., via an actuator such as a knob, pin, or lever. In an embodiment, with articulation assembly 120 in the delivery/closed state, the distal segment 116 can be selectively adjusted (via the pull-wire 190 acting upon the tip 142) in a first direction (e.g. along arrow 522) within the left ventricle, for e.g., to provide adequate space for transition of the articulation assembly 120 from the delivery/closed state to the deployed/ open state. In an embodiment, with articulation assembly 120 in the deployed/open state, the valve prosthesis 501A can be aligned with the native valve region with adjustment of the distal segment 116 via the pull-wire 190 acting upon the tip 142. Accordingly, a clinician can deflect the second atraumatic tip 142 in a first direction (e.g., along arrow 522) to move the arm portion 122 and the valve prosthesis 501A when in the deployed state further into the left ventricle in the direction of arrow 524 and out of the native mitral valve region. Likewise, a clinician can deflect the distal second atraumatic tip 142 in a second direction (e.g., in the direction of arrow 526) to move the arm portion 122 (in the deployed state) and the valve prosthesis 501A in the direction of arrow 528 and into the native mitral valve region.

Once the mitral valve prosthesis 101A is positioned within the mitral valve MV, the mitral valve prosthesis 101A can be deployed for implantation. In one embodiment, the mitral valve prosthesis 101A can include a self-expanding frame that is restrained in a low-profile or compressed configuration during delivery and positioning of the device. The self-expanding frame of the mitral valve prosthesis 101A can be retained in the compressed configuration and controllably released for expansion/implantation, for example, using a cinch device 521 that is only shown in FIG. 5C for ease of illustration. The cinch device 521 can have one or more loops disposed about at least a portion of the self-expanding frame such that constriction or expansion/ removal of the one or more loops controls compression or expansion of the frame. Examples of suitable cinch devices for retaining self-expanding prosthetic frames are described in U.S. Patent Publication No. 2014/0330368, which is incorporated herein by reference in its entirety. Upon successful implantation of the mitral valve prosthesis 101A, the cinch device 130 is fully removed and the delivery catheter 102 is advanced (e.g., in the direction of arrow 516) to disengage the arm portion 122 from the mitral valve region in the direction of arrow 518 and move it further into the left ventricle LV.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery and positioning of the mitral valve prosthesis 101A at the target native valve region. For example, once the articulation assembly 120 is positioned within the left ventricle LV (FIG. 5A), such image guidance technologies can be used to transition the articulation assembly 120 into the open (deployed) state wherein the extension of the elbow portion 124 causes the arm portion 122 to orient the mitral valve prosthesis 101A toward the mitral valve MV such that an inflow region 501A of the mitral valve prosthesis 101A is aligned with the region of coaptation of the leaflets (FIGS. 5B and 5C). In another embodiment, selected outer surfaces of the articulation assembly 120 and the distal segment 116 can be treated such that the echogenicity of the articulation assembly 120 and the distal segment 116 is enhanced. Image guidance technologies can be further used during partial retraction of the delivery catheter 102 in a proximal direction along arrow 512 (e.g., without removing the articulation system 120 from the left ventricle LV) to move the inflow region 501A and/or other portions of the mitral valve prosthesis 101A into position within and/or adjacent to the native mitral valve MV for deployment and implantation (FIG. 5C). Additionally, image guidance technologies can be used to deploy and implant the mitral valve prosthesis 101A within the mitral valve anatomy prior to removal of the delivery catheter 102 from the body of the patient. In some embodiments, image guidance components (e.g., IVUS, OCT) can be coupled to the distal segment 116 of the delivery catheter 102 to provide three-dimensional images of the vasculature proximate to the target heart valve region to facilitate positioning, orienting and/or deployment of the mitral valve prosthesis 101A within the heart valve region.

To adjust the position of the mitral valve prosthesis 101A with respect to the mitral valve MV, a clinician can incrementally advance (e.g., push) or retract (e.g., pull) the handle component 104 (FIG. 3) of the delivery catheter 102 to adjust the position of the arm portion 122 within the left ventricle LV and/or within the mitral valve MV. Accordingly, a clinician can advance the delivery catheter 102 in a distal direction (e.g., along arrow 516) to move the arm portion 122 when in the deployed state further into the left ventricle LV (FIG. 5B). Likewise, a clinician can retract the delivery catheter 102 in a proximal direction (e.g., in the direction of arrow 512) to move the arm portion 122 (in the deployed state) in the direction of arrow 514 and into the native mitral valve region (FIG. 5C). Referring to FIG. 5C, after the mitral valve prosthesis 101A is allowed to expand (not shown), the delivery system 100 can still be connected to the mitral valve prosthesis 101A (e.g., system eyelets, not shown, are connected to the device eyelets) so that the operator can further control the placement of the mitral valve prosthesis 101A as it returns toward the expanded configuration. Alternatively, the mitral valve prosthesis 101A may not be connected to the delivery system 100 by anything other than the cinch device 521, such that the mitral valve prosthesis 101A deploys and is fully released from the delivery system 100 once the cinch device 521 is removed.

Further adjustments with respect to the orientation of the arm portion 122 (and thereby the mitral valve prosthesis 101A) can be made by adjusting the extension angle $A_{EX}$ via actuation of the tether device 130. Referring to FIGS. 5B and 5C, tensioning (e.g., retracting) and relaxing (e.g., advancing) the tether line 132 can decrease and increase the extension angle $A_{EX}$, respectively, to alter the trajectory of the arm portion 122 when subsequently moved in a upward direction along arrow 514. Further adjustment of the tether line 132 can be made once the mitral valve prosthesis 101A is positioned within the native mitral valve MV and during the deployment of the mitral valve prosthesis. With reference to FIGS. 5A-5C together, a clinician can, in real time, determine a desired target point at which to position the mitral valve prosthesis 101A within the mitral valve MV (e.g., at a center of the valve, at a region of leaflet coaptation, etc.) and retract/advance the delivery catheter 102 to move the arm portion 122 along arrows 514 and/or 518, and retract or advance the tether line 132 to adjust the extension angle $A_{EX}$ and thereby adjust the trajectory of a subsequently advanced arm portion 122.

Following delivery, placement and implantation of the mitral valve prosthesis 101A within the mitral valve MV (or other desired valve location), the delivery catheter 102 and remaining guidewire (if any) can be removed from the heart 10 and out of the body of the patient. For example, once successful implantation of the mitral valve prosthesis 101A is achieved, the articulation assembly 120 can be returned to the closed (delivery) state via flexion of the elbow portion 124 (e.g., retraction of the tether line 132) and the distal segment 116 of the delivery catheter 102 can be retracted proximally through the vasculature and removed from the body, as would be understood by one of skill in the art. In some instances, a protective sheath, other than the outer tubular component 106, may be advanced at least partially over the distal segment 116 of the delivery catheter 102 to protect the vascular structure during removal of the delivery catheter 102.

Figure 6A:
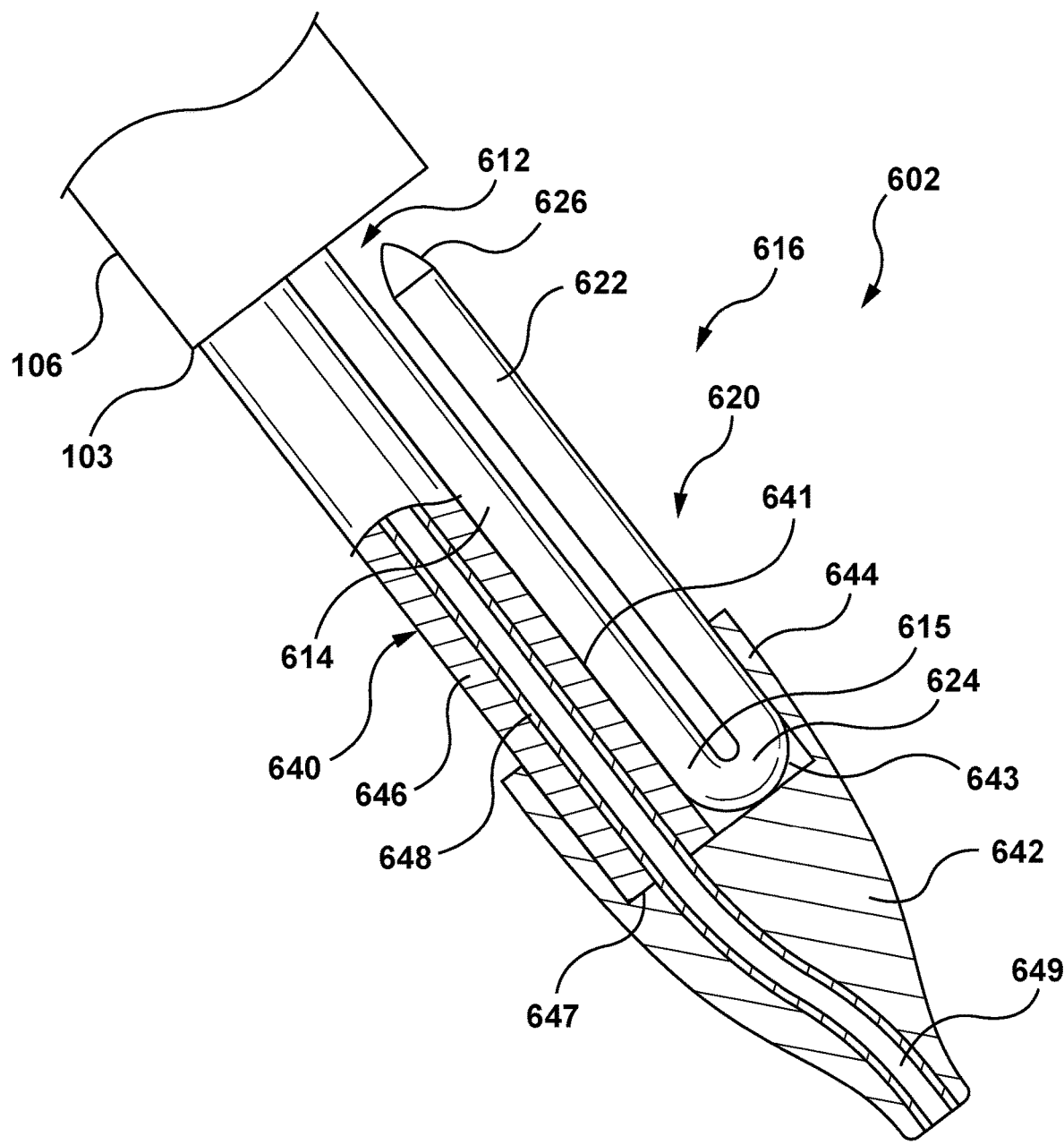
FIGS. 6A and 6B are enlarged partial cross-sectional views of a distal segment of a delivery catheter for use with the heart valve prosthesis delivery system of FIG. 3 shown in delivery and deployed configurations, respectively, and in accordance with another embodiment hereof.
Figure 6B:
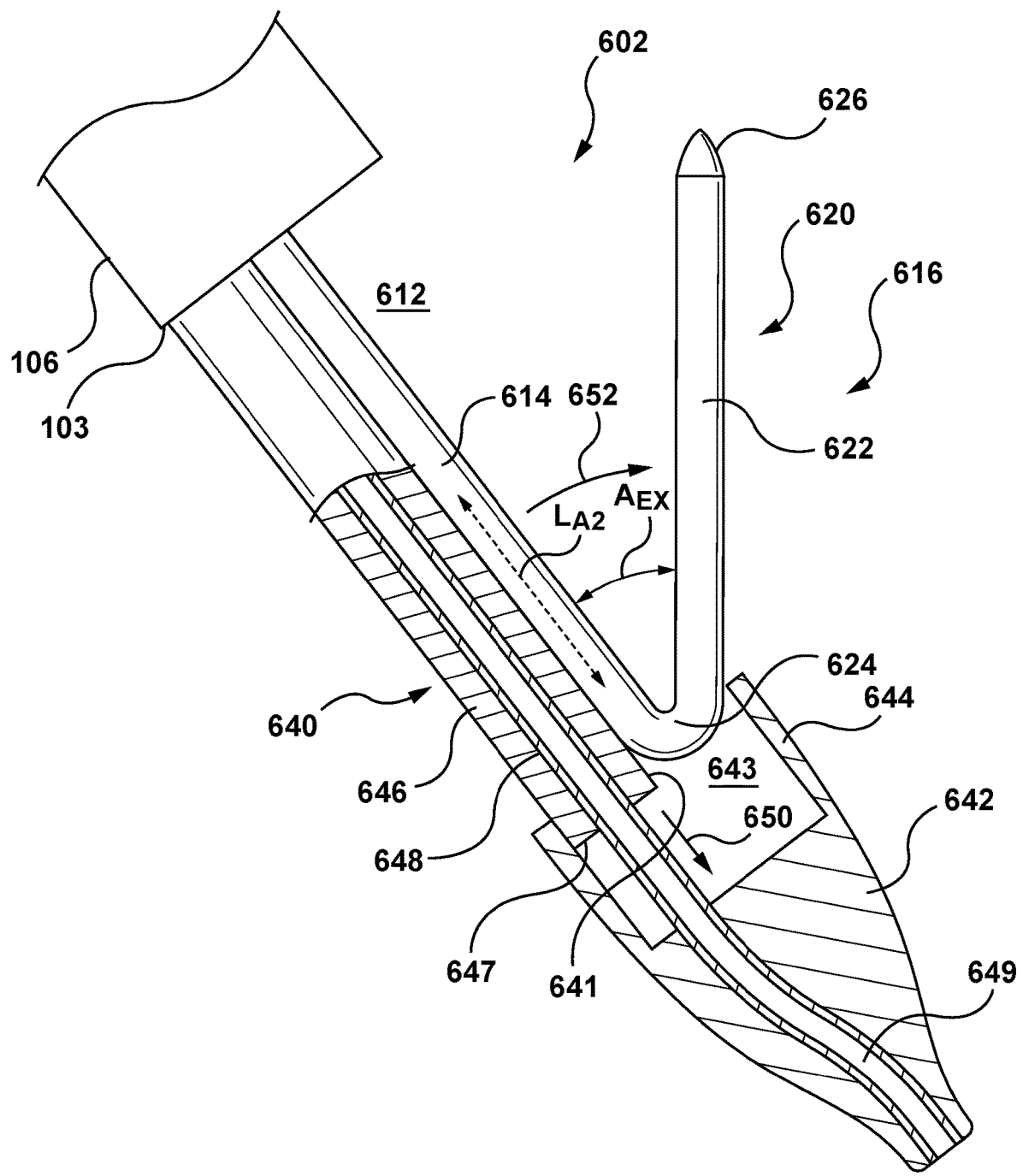

Additional Embodiments of Delivery Catheters and Delivery Catheters Having Articulation Assemblies FIGS. 6A and 6B are enlarged partial sectional views of a distal segment 616 of a delivery catheter 602 for use with the heart valve prosthesis delivery system 100 of FIG. 3 shown in delivery and deployed states, respectively, and in accordance with another embodiment hereof. The delivery catheter 602 includes features generally similar to the features of the delivery catheter 102 described above with reference to FIGS. 4A-5C. For example, the delivery catheter 602 includes a first tubular component 614 and an articulation assembly 620 at a distal end 615 of the first tubular component 614, wherein the articulation assembly 620 is reversibly receivable within a recessed segment or space 612 of the distal segment 616. The articulation assembly 620, shown in FIG. 6A in a closed (delivery) state and in FIG. 6B in an open or outwardly angled (deployed) state, includes an arm portion 622, having an atraumatic tip or end 626, configured to carry a prosthetic valve device (not shown) and an elbow or hinge portion 624 coupling the arm portion 622 to the first tubular component 614. However, in the embodiment shown in FIGS. 6A and 6B, the delivery catheter 602 does not include a tether device 130 (FIGS. 4A-5C) for actuating the transition of the articulation assembly 620 between the open/delivery and closed/deployed states.

In the embodiment illustrated in FIGS. 6A and 6B, the delivery catheter 602 includes a second tubular component 640 coupled to a distal tip portion 642 having a proximal facing recess 643 or bore that is configured to receive the elbow portion 624 when in flexion (e.g., in the delivery state). Accordingly, the elbow portion 624 is restrained in flexion between an outer wall 641 of the second tubular member 640 and a flange 644 that forms the recess 643 within the distal tip portion 642. As described above with respect to the articulation assembly 120 shown in FIGS. 4A-5C, the articulation assembly 620 can be comprised of a material (e.g., nitinol) and processed to have a shape-set or shape memory, such that when not restrained, will return the articulation assembly 620 to a non-biased state. Accordingly, the elbow portion 624 can be in flexion when restrained within the recess 643 (FIG. 6A), and in a degree of extension or outwardly angled when restraint on the articulation assembly 620 is at least partially removed (FIG. 6B).

Referring to FIG. 6A, the second tubular component 640 can include an outer tubular member 646 and an inner tubular member 648 that resides within the outer tubular member 646 and which extends distally beyond a terminal end 647 of the outer tubular member 646 and through the distal tip portion 642. The inner tubular member 648 can be longitudinally translatable relative to the outer tubular member 646 to advance or retract the distal tip portion 642 with respect to the distal end 647 of the outer tubular member 646. The inner tubular member 648 may be affixed to the distal tip portion 642 via adhesive or other suitable technique. Furthermore, the inner tubular member 648 can define a guidewire lumen 649 through the second tubular component 640 and the distal tip portion 642 to facilitate OTW or RX delivery of the delivery catheter 602 to a target location (e.g., within the left ventricle LV).

In an alternative arrangement, the second tubular component 640 does not include the inner tubular member 648 and the distal tip portion 642 can be attached directly to the terminal end 647 of the outer tubular member 646. In this arrangement, the second tubular component 640 can be longitudinally translatable relative to the delivery catheter 602 within the outer tubular component 106 of the delivery catheter 602, for example, to advance or retract the distal tip portion 642 with respect to the articulation assembly 620, thereby releasing or restraining the self-expanding elbow portion 624 of the articulation assembly 620 by corresponding movement thereof.

Referring to FIGS. 6A and 6B together, the distal tip portion 642 is configured to advance distally along arrow 650 and with respect to the second tubular component 640 and/or the delivery catheter 602 such that the elbow portion 624 is at least partially released from the restraint or confines of the recess 643. The elbow portion 624 is released from restraint proportionally to the distance the distal tip portion 642 outwardly moves in the direction of arrow 650. Stated another way, the arm portion 622 moves outwardly in the direction of arrow 652 (e.g., away from a longitudinal axis $L_{A2}$ of the first tubular member 614) as the distal tip portion 642 is advanced in the direction of arrow 650 (FIG. 6B). Accordingly, the extension angle $A_{EX}$ increases as the articulation assembly 620 is transitioned from the closed (delivery) state (e.g., wherein the extension angle $A_{EX}$ is substantially 0 degrees) to the open (deployed) state. When orienting the arm portion 622 to deliver a prosthetic valve device 101 to the mitral valve using a retrograde approach, the extension angle $A_{EX}$ can be less than about 90 degrees. Once deployed, the extension angle $A_{EX}$ of the articulation assembly 620 may be incrementally adjusted by advancing or retracting the distal tip portion 642 until the prosthetic valve device (not shown) is aligned with the native heart valve (e.g., the mitral valve). Returning the delivery catheter 602 from the deployed configuration to the delivery configuration can be accomplished by longitudinally translating the inner tubular member 648 in a proximal direction such that the distal tip portion 642 is retracted. The elbow portion 624 of the articulation assembly 620 may be recaptured within the proximal facing recess 643 such that the arm portion 622 returns to a position generally parallel to the first tubular component 614.

Figure 7A:
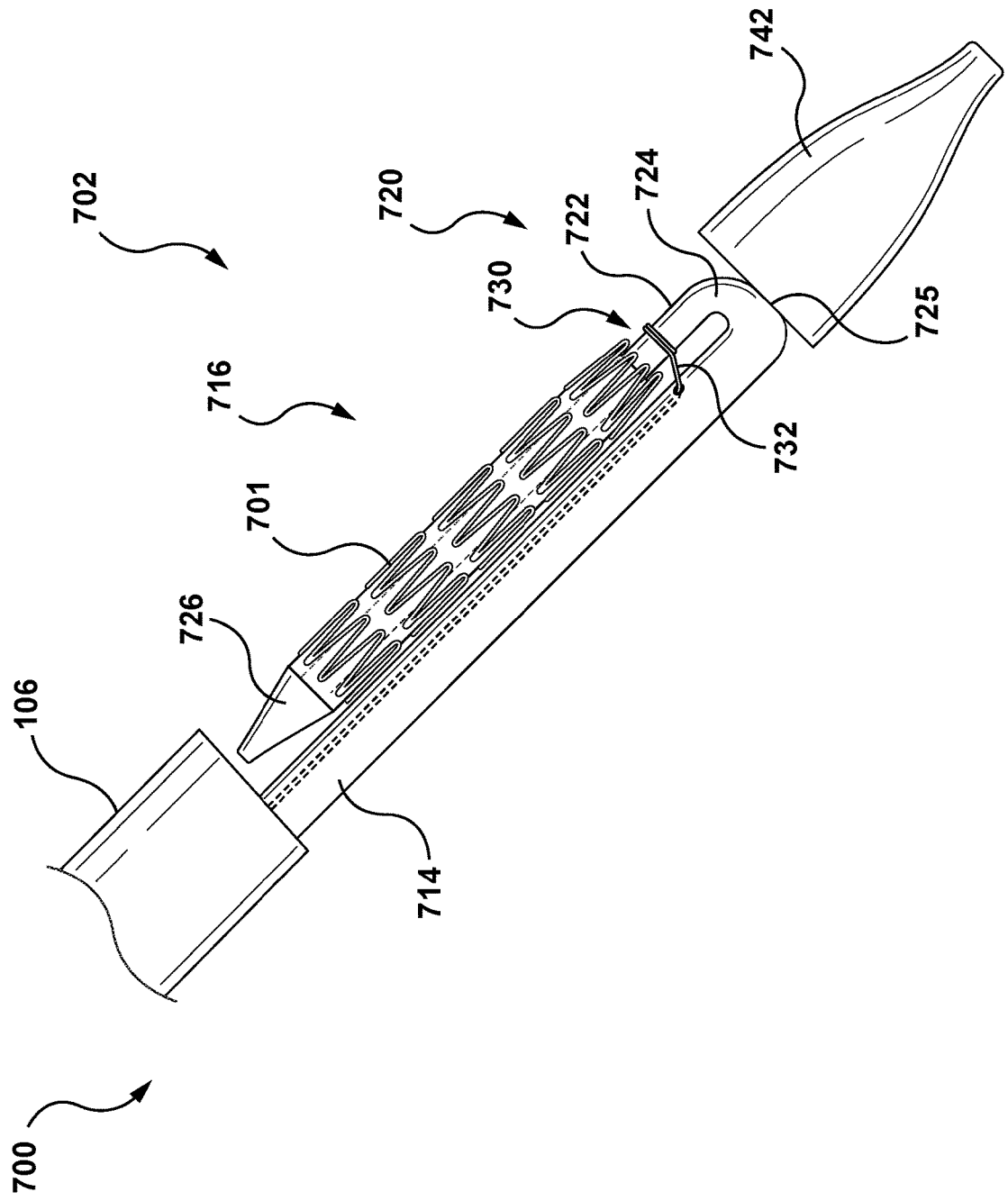
FIG. 7A is a partial side view of a distal segment of a delivery catheter for use with a heart valve prosthesis delivery system, shown in a delivery configuration, and in accordance with yet another embodiment hereof.
Figure 7C:
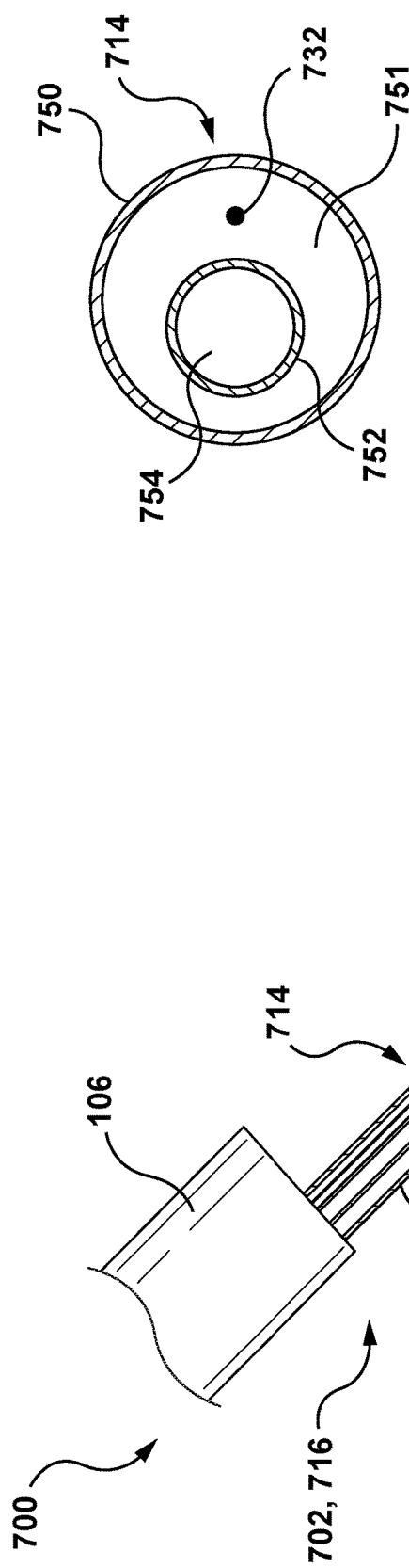
FIG. 7C is an enlarged cross-sectional view of the distal segment of the delivery catheter of FIG. 7B at plane line C-C.
Figure 7B:
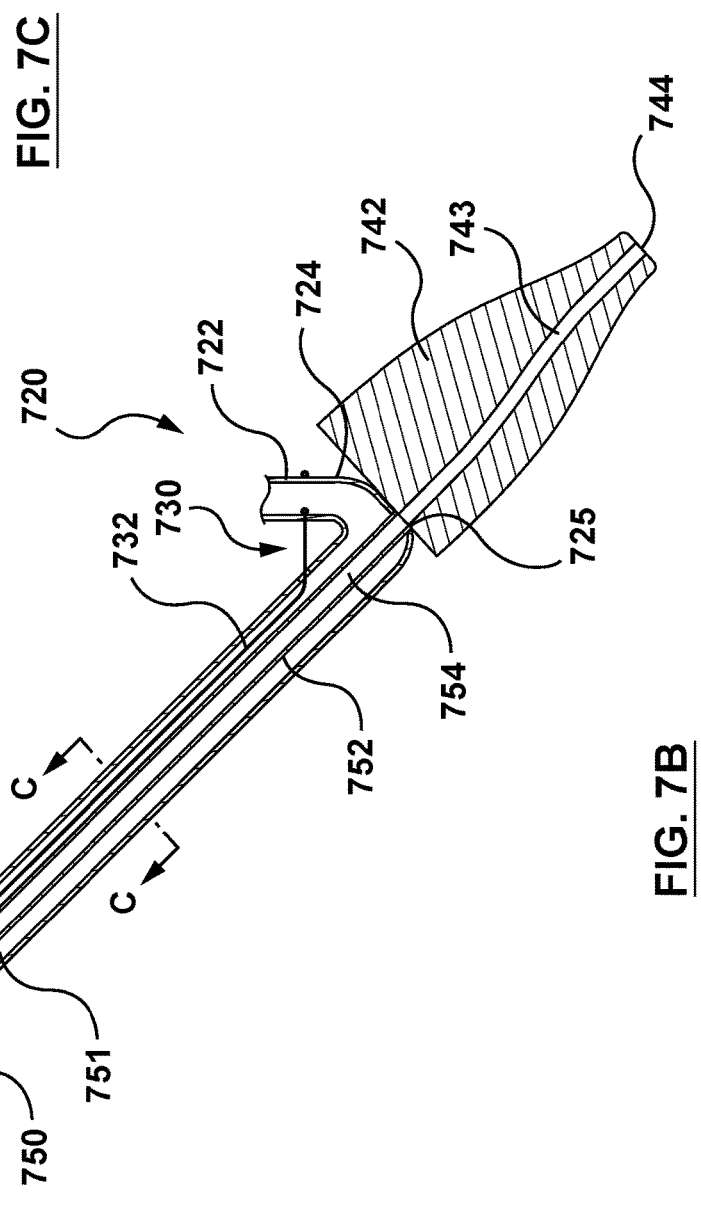
FIG. 7B is a partial cross-sectional view of the delivery catheter of FIG. 7A shown in a deployed state, and in accordance with an embodiment hereof.

FIG. 7A is a partial side view of a distal segment 716 of a delivery catheter 702 for use with a heart valve prosthesis delivery system 700 shown in a delivery configuration and in accordance with yet another embodiment hereof. FIG. 7B is a partial sectional view of the delivery catheter 702 of FIG. 7A shown in a deployed configuration. The delivery catheter 702 includes features generally similar to the features of the delivery catheter 102 described above with reference to FIGS. 4A-5C. For example, the delivery catheter 702 includes an elongated tubular component 714 and an articulation assembly 720 at a distal end of the elongated tubular component 714. The delivery catheter 702 also includes a tether device 730 generally similar to the tether device 130 (FIGS. 4A-5C) for actuating the transition of the articulation assembly 720 between the closed/delivery (FIG. 7A) and open/deployed (FIG. 7B) states. However, in the embodiment shown in FIGS. 7A and 7B, the delivery catheter 702 does not include a second tubular component 140 (FIGS. 4A-5C).

In the embodiment illustrated in FIGS. 7A and 7B, the delivery catheter 702 includes a second atraumatic tip 742 coupled to a distal end portion 725 of the delivery catheter 702 to prevent intravascular trauma during delivery of the prosthetic valve device 101 to a target location. The second atraumatic tip 742 can be a separate component that may be affixed to the distal end portion 725 of the delivery catheter 702 via adhesive, crimping, over-molding, or other suitable techniques, and can be formed from the same or similar materials as discussed previously with respect to the first and second atraumatic tips 126, 142. In some instances, the distal end portion 725 of the delivery catheter 702 may also generally correspond to at least a portion of the elbow portion 724 of the articulation assembly 720.

Referring to FIG. 7B, the elongated tubular component 714 can include an outer tubular member 750 and an inner tubular member 752 that resides within the outer tubular member 750. An end segment of the outer tubular member 750 may form an elbow portion 724 and an arm portion 722 of the delivery catheter 702, as similarly described above with reference to tubular component 114. FIG. 7C is an enlarged cross-sectional view of the distal segment 716 of the delivery catheter 702 of FIG. 7B at plane line C-C. Referring to FIGS. 7B and 7C together, the inner tubular member 752 can also have a generally hollow body that extends between the handle component 104 (FIG. 3) and the distal segment 716 of which can define therethrough a guidewire lumen 754 configured to slidably receive a guidewire (not shown) for delivering the delivery catheter 702 to a target location in the heart. As shown in FIG. 7B, the guidewire lumen 754 generally aligns with a passage 743 through the second atraumatic tip 742 for facilitating an OTW or RX delivery of the delivery catheter 702 to a target location. For example, the second atraumatic tip 742 may define a distal opening 744 for receiving a guidewire for tracking of the delivery catheter 702 over a guidewire using OTW or RX techniques. A lumen 751 defined by the outer tubular member 750 accommodates the inner tubular member 752 as well as other features of the delivery catheter 702 such as, for example, tether lines 732 of the tether device 730. In other arrangements, not shown, the lumen 751 may also accommodate other structures such as a guidewire (not shown) that is advanced through the articulation assembly 720 (e.g., the elbow portion 724 and the arm portion 722) and exits the first atraumatic tip 726 to facilitate delivery of the prosthetic valve device 101 within the target native valve (e.g., mitral valve).

Figure 8:
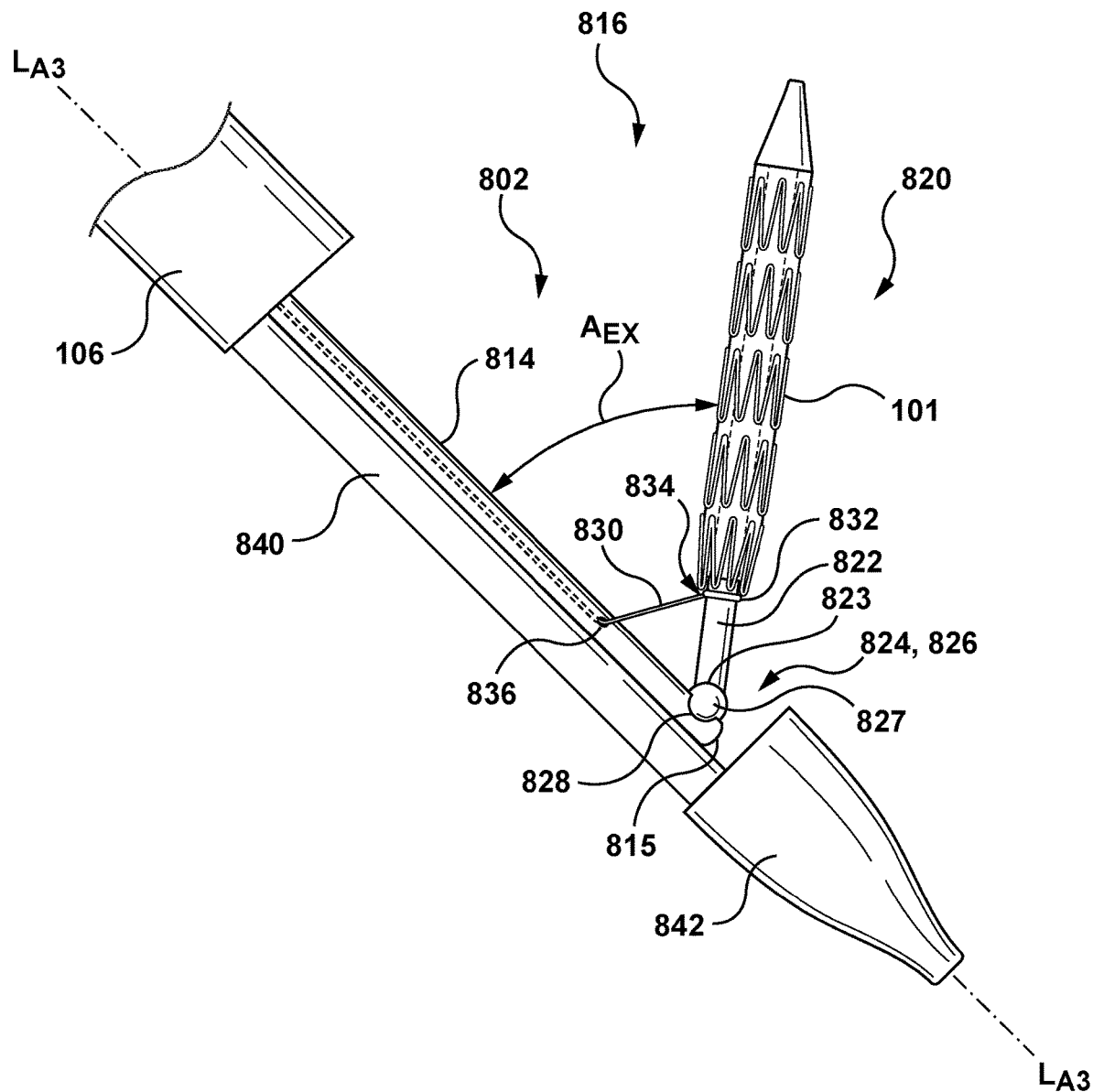
FIG. 8 is a partial side view of a distal segment of a delivery catheter for use with the heart valve prosthesis delivery system of FIG. 3 in a deployed configuration in accordance with a further embodiment hereof.
Figure 9:
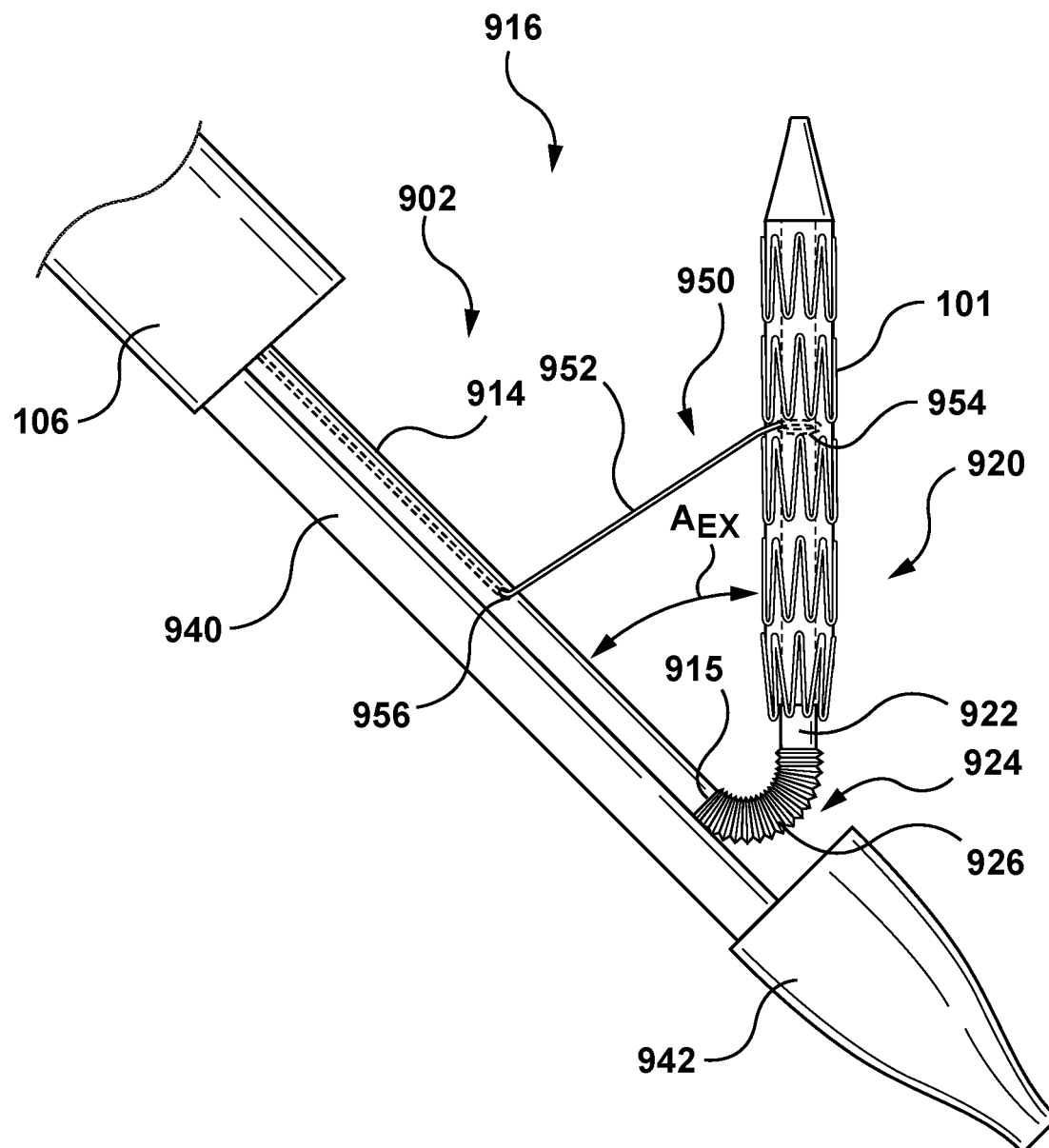
FIG. 9 is a partial side view of a distal segment of a delivery catheter for use with the heart valve prosthesis delivery system of FIG. 3 in a deployed configuration in accordance with yet a further embodiment hereof.

FIGS. 8 and 9 are side views of distal segments 816, 916 of delivery catheters 802, 902 for use with the heart valve prosthesis delivery system 100 of FIG. 3 shown in deployed configurations in accordance with further embodiments hereof. The delivery catheters 802, 902 include features generally similar to the features of the delivery catheter 102 described above with reference to FIGS. 4A-5C. For example, the delivery catheters 802, 902 include a first tubular component 814, 914 and an articulation assembly 820, 920 at a distal end 815, 915 of the first tubular component 814, 914. The delivery catheters 802, 902 also include a second tubular component 840, 940 and a second atraumatic tip 842, 942 generally similar to the second tubular component 140 and the second atraumatic tip 142 of the delivery catheter 102 (FIGS. 4A-5C).

The articulation assemblies 820, 920, shown in FIGS. 8 and 9 in an open or angled outward (deployed) state (e.g., when the delivery catheters 802, 902 are in deployed configurations), include an arm portion 822, 922 configured to carry a prosthetic valve device 101 and an elbow portion 824, 924 coupling the arm portion 822, 922 to the first tubular component 814, 914. However, in the embodiments shown in FIGS. 8 and 9, the articulation assemblies 820, 920 do not have a shape memory, or stated another way, the elbow portions 824, 924 are not shape-set to return to an open or outwardly angled state when unrestrained.

In the embodiment illustrated in FIG. 8, the elbow portion 824 comprises a hinged joint 826, such as a ball-and-socket hinge mechanism. As shown, a ball component 827 is coupled/attached to a proximal end 823 of the arm portion 822, and a corresponding recessed socket 828 is formed a terminal end of the first tubular component 814 to accommodate the ball component 827. Accordingly, the ball component 827 may rotate within the recessed socket 828 to transition the arm portion 822 along an extension path between closed and opened states. Referring to FIG. 8, the arm portion 822 is reversible between an outward extended or open state and an inward closed state by translation of one or more elongated elements with sufficient columnar stiffness to act as push/pull mechanisms, such as one or more sufficiently stiff wire 830. The wire 830 is at least partially disposed within the first tubular component 814 of the delivery catheter 802. The wire 830 can be attached to a cuff or collar 832 about the arm portion 822 to form an attachment point 834 for affecting the position of the arm portion 822 with respect to the first tubular component 814. In one embodiment, the wire 830 extends from the handle component 104 (FIG. 3) and can be deployable via remote actuation, e.g., via an actuator 108 (FIG. 3). The wire 830 exits the first tubular component 814 through a hole 836 or recess formed in the first tubular component 814 and extends to the attachment point 834 (e.g., the wire 830 is coupled to the collar 832) on the arm portion 822.

When transitioning of the articulation assembly 820 from the closed (delivery) state to the open (deployed) state is desired, the wire 830 can be advanced via the actuator 108, causing extension of the elbow portion 824 by pushing the arm portion 822 in a direction away from the first tubular component 814. Once deployed, adjustment of the extension angle $A_{EX}$ is possible by retracting or advancing the wire 830 until a desired extension angle $A_{EX}$ is achieved that orients the prosthetic valve device 101 for deployment in a target native valve. Likewise, the articulation assembly 820 transitions from the open (deployed) state to the closed (delivery) state when the wire 830 is retracted, causing flexion of the elbow portion 824 by activation of the hinged joint 826, until the arm portion 822 is generally parallel with a longitudinal axis $L_{A3}$ (e.g., the extension angle $A_{EX}$ is substantially 0 degrees).

Referring back to the embodiment illustrated in FIG. 9, the elbow portion 924 comprises a flexible bellows connector 926 having concertinaed sides to allow expansion and contraction as well as lateral and angular movement. In one embodiment, the bellows connector 926 allows the arm portion 922 to be reversibly opened or closed using a pressurized fluid source such as an inflation fluid source 107 (FIG. 3) that can be operatively coupled to the delivery catheter 902. For example, the first tubular component 914 can define and/or house an inflation lumen (not shown) through which pressurized air or other fluid can flow. As the pressurized fluid flows through the bellows connector 926, a partial pressure increase in the flexible region can cause outward extension of the bellows connector 926, thereby transitioning the arm portion 922 into an open (delivery) state. Once deployed, adjustment of the extension angle $A_{EX}$ may be obtained by reducing or increasing fluid pressure within the bellows connector, e.g., by controlling fluid flow from the inflation fluid source 107 (FIG. 3). Likewise, the articulation assembly 920 can be configured to transition from the open (deployed) state to the closed (delivery) state when fluid flow is ceased. In certain arrangements, the bellows connector 926 can be accompanied by a hinge mechanism (not shown) along the length of the bellows connector 926 which is strong enough to accept the pressure generated thrust but will allow angular movement in a single plane (e.g., along a desired extension path). In an alternative arrangement, the delivery catheter 902 can include a wire mechanism similar to the wire 830 and collar 832 described with respect to the embodiment of FIG. 8 instead of or in addition to the pressurized fluid source for extending the bellows connector 926 during deployment of the articulation assembly 920.

While the elbow portions 824/924 are described with reference to FIGS. 8-9 as either a hinged joint 826 or a flexible bellows connector 926, this is not meant to be limiting, and the elbow portion may be comprised of additional designs including, but not limited to a wound coil, or other designs suitable for the purposes described herein.

Further illustrated in FIG. 9 is a tether device 950 for returning the arm portion 922 to a closed (delivery) state. As described above with respect to the method steps for deployment of the mitral valve prosthesis 101A (FIGS. 5A-5C), the tether device 950 can have a tether line 952 that has a loop 954 that is disposed about a midportion of the arm portion 920. The tether line 952 can extend from a hole 956 in the first tubular component 914 and to the handle component 104 (FIG. 3) where it is actuatable via remote actuation, e.g., via an actuator 108 (FIG. 3). As well, as previously described above, the prosthetic valve device may be held in its compressed delivery state by a cinch device (not shown), wherein examples of suitable cinch devices for retaining self-expanding prosthetic frames are described in U.S. Patent Publication No. 2014/0330368, which is incorporated herein by reference in its entirety. Upon successful implantation of the prosthetic valve device 101, any cinch device is fully removed.

Embodiments of delivery systems, delivery catheters, and associated methods in accordance with the present technology incorporating balloon-expandable prosthetic valve devices are described below with reference to FIGS. 3 and 10A-12C.

Figure 10A:
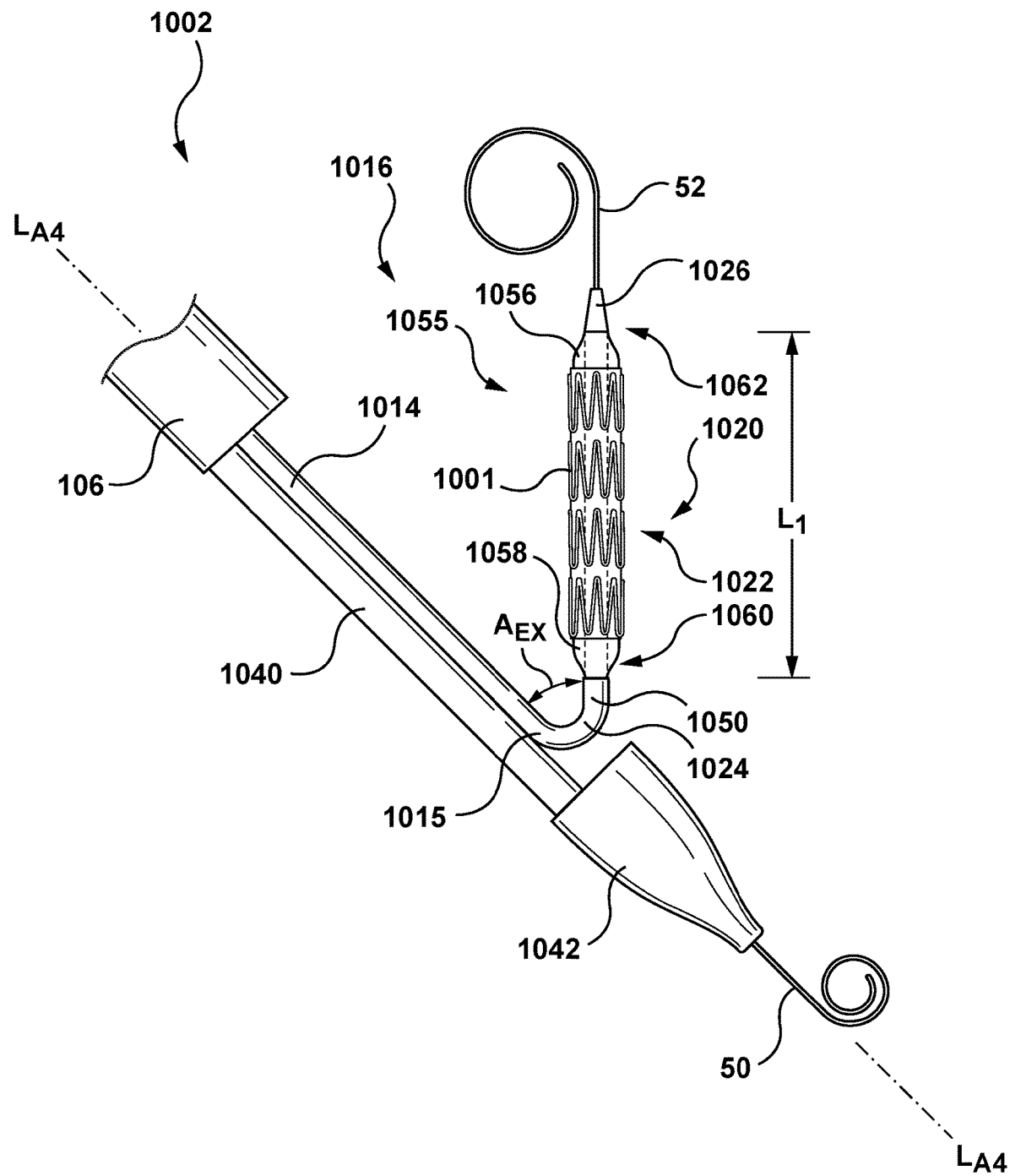
FIG. 10A is a partial side view of a distal segment of a delivery catheter for use with the heart valve prosthesis delivery system of FIG. 3 shown in a partially deployed configuration in accordance with another embodiment hereof.
Figure 10B:
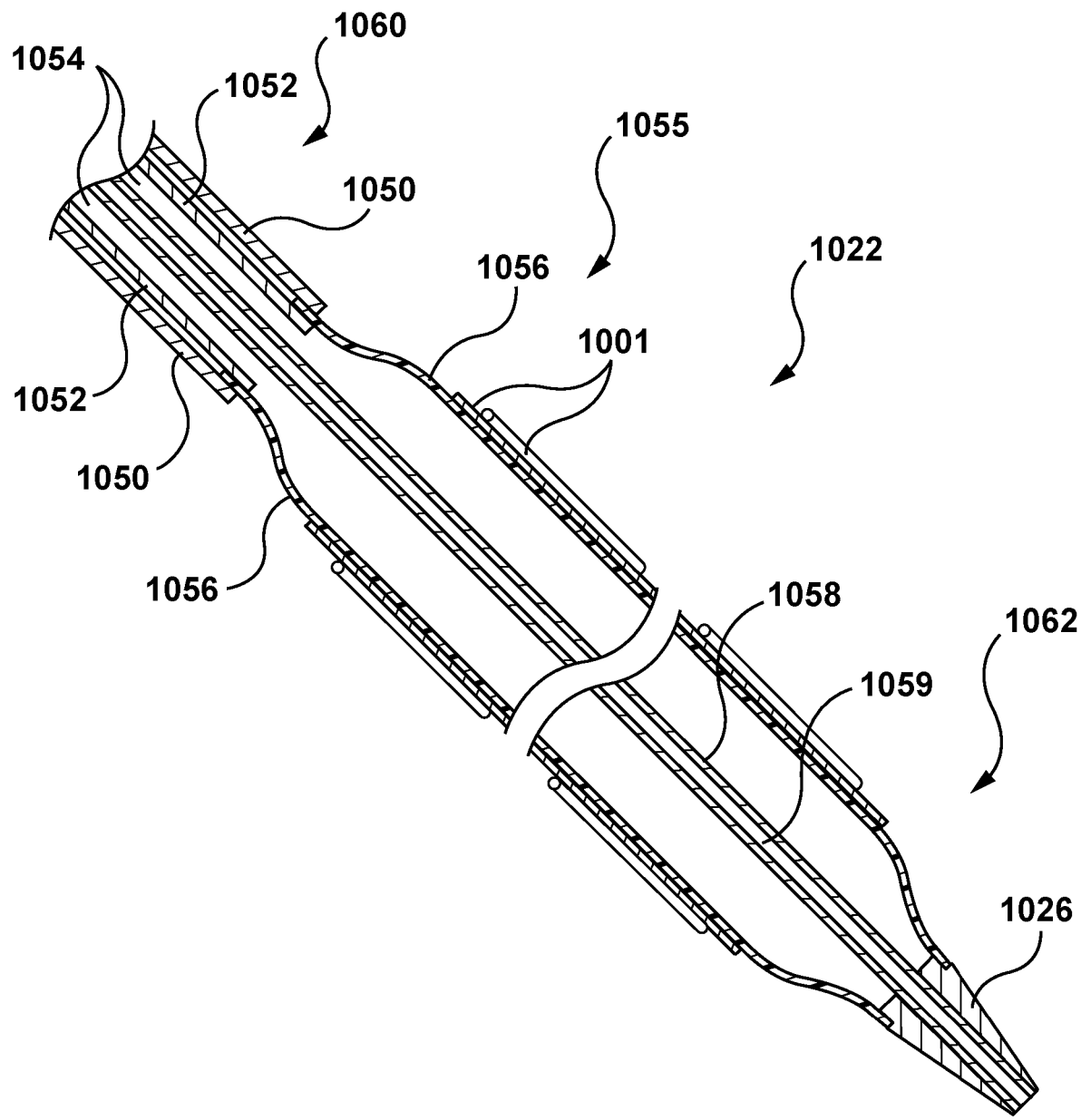
FIG. 10B is a sectional side view of an arm portion of the delivery catheter of FIG. 10A in accordance with an embodiment hereof.
Figure 10C:
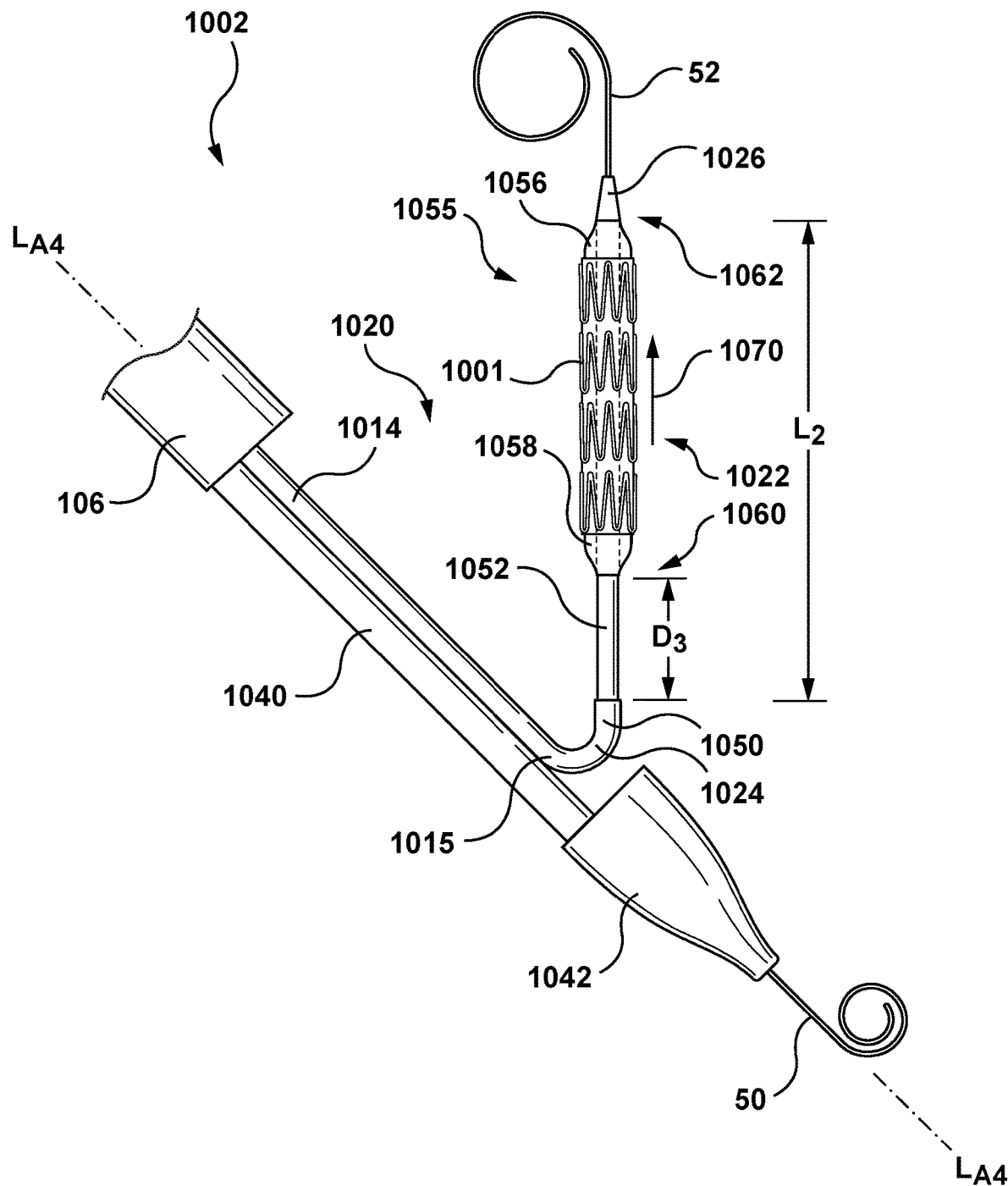
FIG. 10C is a partial side view of the distal segment of the delivery catheter of FIG. 10A shown in a deployed configuration in accordance with an embodiment hereof.

FIGS. 10A-10C illustrate a distal segment 1016 of a delivery catheter 1002 for use with the heart valve prosthesis delivery system 100 of FIG. 3 in accordance with another embodiment hereof. Referring to FIG. 10A, the delivery catheter 1002 includes features generally similar to the features of the delivery catheter 102 described above with reference to FIGS. 4A-5C. For example, the delivery catheter 1002 includes a first tubular component 1014 and an articulation assembly 1020 at a distal end 1015 of the first tubular component 1014. The delivery catheter 1002 also include a second tubular component 1040 and a second atraumatic tip 1042 generally similar to the second tubular component 140 and the second atraumatic tip 142 of the delivery catheter 102 (FIGS. 4A-5C). As shown in FIG. 10A, the second tubular component 1040 and the second atraumatic tip 1042 provide a guidewire lumen (not shown) therethrough for slidably receiving a guidewire 50 for OTW or RX delivery of the delivery catheter 1002.

The articulation assembly 1020 further includes an elbow portion 1024 which couples an arm portion 1022 to the first tubular component 1014. In one embodiment, the articulation assembly 1020 is shape set to return to an open state such that a restraint mechanism (e.g., tether device 130 shown in FIGS. 4A-5C, etc.) is used to retain the elbow portion 1024 in a state of flexion in which the arm portion 1022 is generally parallel to the first tubular component 1014 (not shown). In another arrangement, the elbow portion does not have a shape memory (is not shape set) and the elbow portion 1024 can be a hinge mechanism that is actuated by a wire, fluid pressure, or other mechanism as previously described.

The delivery catheter 1002 differs from the delivery catheter 102 for at least the reason that i) the articulation assembly 1020 deploys in two phases, and ii) the arm portion incorporates a balloon assembly 1055 over which a balloon-expandable prosthetic valve device 1001 is disposed and crimped in a low profile delivery configuration, wherein the balloon assembly 1055 is configured for deploying the balloon-expandable prosthetic valve device 1001 within the native valve region (e.g., mitral valve) as described below. In a first phase of deployment, the arm portion 1022 angles away from the longitudinal axis $L_{A4}$ of the first tubular component 1014 by an extension angle $A_{EX}$ (FIG. 10A). In a second phase of deployment, a length $L_1$ of the arm portion 1022 (FIG. 10A) is extended to a deployed length $L_2$ (FIG. 10C). The deployed length $L_2$ facilitates positioning of the balloon-expandable prosthetic valve device 1001 within the native valve region, such as the mitral valve.

The arm portion 1022 is configured to carry the balloon-expandable prosthetic valve device 1001 along the length $L_1$ thereof (FIG. 10A). FIG. 10B is a sectional side view of the arm portion 1022 of the articulation assembly 1020 of FIG. 10A. Referring to FIGS. 10A and 10B together, the arm portion 1022 includes an outermost tubular member 1050 and an inflation tubular member 1052 residing in the outermost tubular member 1050. The outermost tubular member 1050 can be integral with the elbow portion 1024 and the first tubular component 1014 as shown in FIG. 10A. In other arrangements, the outermost tubular member 1050 can be a separate component that is coupled to the elbow portion 1024. The inflation tubular member 1052 extends from the handle component 104 (FIG. 3) of the delivery catheter 1002, through the first tubular component 1014, the elbow portion 1024, and to a proximal arm segment 1060. As can best be seen in FIG. 10C, the inflation tubular member 1052 can be longitudinally translatable relative to the outermost tubular member 1050 to extend or shorten the length $L_1, L_2$ of the arm portion 1022 at the proximal arm segment 1060. Stated another way, advancement of the inflation tubular member 1052 with respect to the outermost tubular member 1050 advances the prosthetic valve device 1001 in a non-axial direction with respect to the longitudinal axis $L_{A4}$ of the first tubular component 1014. In an alternative embodiment, the inflation tubular member 1052 may be rotatable relative to the outermost tubular member 1050. The inflation tubular member 1052 may be rotatable via remote actuation, e.g., via an actuator such as a knob, pin, or lever carried by the handle component 104. In the deployed/open state, the valve device 101 can be rotationally aligned with the native valve region with rotational adjustment of the inflation tubular member 1052.

Referring back to FIG. 10B, the delivery catheter 1010 further includes an inflation lumen 1054 along the length of the inflation tubular member 1052, and which begins at the handle component 104 (FIG. 3) and terminates in fluid communication with a balloon 1056 of the balloon assembly 1055. The inflation lumen 1054 facilitates pressurized air or other fluid flow from the inflation fluid source 107 (FIG. 3) to the balloon 1056 of the arm portion 1022. The balloon 1056 may be an inflatable device or vessel over which the balloon-expandable prosthetic valve device 1001 is positioned. For example, the prosthetic valve device 1001 can be crimped on (e.g., around) the unexpanded balloon 1056 on the arm portion 1022. The balloon 1056 can be attached to the inflation tubular member 1052 at the proximal arm segment 1060 as shown in the FIG. 10B. The balloon 1056 can further be attached to a first atraumatic tip 1026 at a distal arm segment 1062 to provide a sealed containment vessel for fluid expansion and deployment of the balloon-expandable prosthetic valve device 1001. The balloon 1056 may be affixed to the inflation tubular member 1052 at the proximal arm segment 1060 and/or to the first atraumatic tip 1026 at the distal arm segment 1062 via adhesive, crimping, over-molding, or other suitable techniques. As shown in FIG. 10C, during deployment as the inflation tubular member 1052 is advanced by a distance $D_3$ with respect to the outermost tubular member 1050 for extending the length $L_1$ (FIG. 10A) of the arm portion 1022 to the extended length $L_2$ (FIG. 10C), the balloon 1056, the prosthetic valve device 1001 and the first atraumatic tip 1026 are moved in the direction of the arrow 1070 to facilitate positioning of the prosthetic valve device 1001 within a target heart valve.

Optionally, an innermost tubular member 1058 can reside within the inflation tubular member 1052 and extend from the handle component 104 (FIG. 3) of the delivery catheter 1010 through the balloon assembly 1055 and first atraumatic tip 1026 to provide a guidewire lumen 1059 therethrough (FIG. 10B). Referring back to FIGS. 10A and 10C, a guidewire 52 can be received through the guidewire lumen 1059 (FIG. 10B) to facilitate positioning of the prosthetic valve device 1001 within the target heart valve during deployment. Operatively, during deployment of the balloon-expandable prosthetic valve device 1001, pressurized fluid from the inflation fluid source 107 can flow through the inflation lumen 1054 to expand the balloon 1056 sufficiently to fully deploy the prosthetic valve device 1001 within the native valve region for implantation.

Figure 10D:
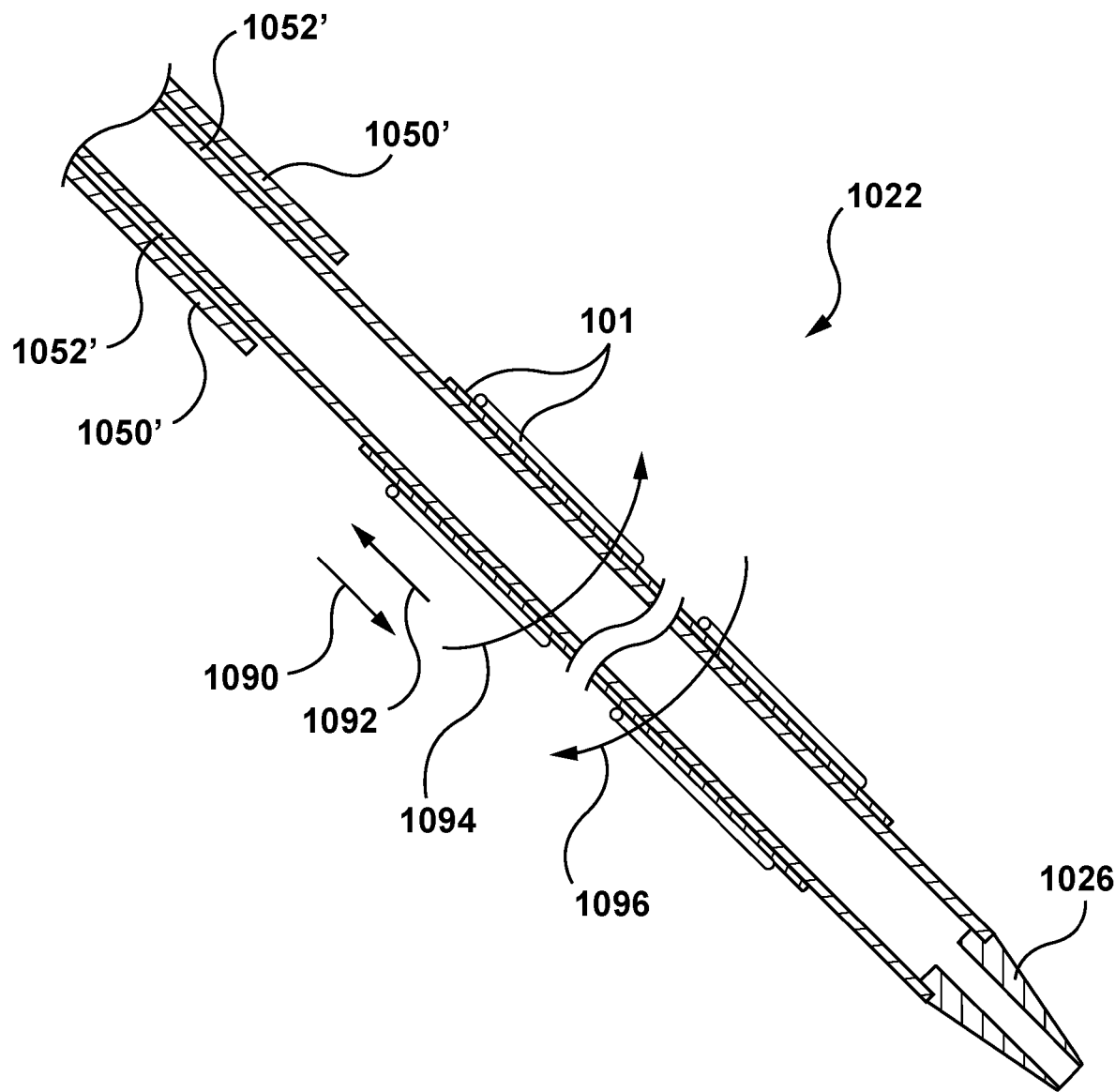
FIG. 10D is a sectional side view of an arm portion of a delivery catheter, which is similar to the one shown in FIG. 10A, in accordance with another embodiment hereof.

FIG. 10D illustrates a modified delivery catheter 1002 with the self-expanding prosthetic valve device 101 held on a distal arm portion 1022' in its compressed, delivery state (by a cinch device or one or more loops of a suture/sutures) in accordance with another embodiment hereof. Referring to FIG. 10D, the modified delivery catheter 1002 includes features generally similar to the features of the delivery catheter 102 described above with reference to FIGS. 4A-5C, as well as some of the features thereof described with reference to FIGS. 10A-10C. The modified delivery catheter 1002 includes a distal member 1052' of the arm portion 1022' that is longitudinally translatable and/or rotatable relative to an outermost tubular member 1050'. The distal member 1052' of the arm portion 1022'is longitudinally translatable and/or rotatable via remote actuations, e.g., via actuators such as knobs, pins, or levers carried by the handle component 104. In the deployed/open state, the valve device 101 can be longitudinally and/or rotationally aligned with the native valve region. For example, movement of the distal member 1052' in a distal or proximal direction (along arrows 1090 and 1092 respectively) translates to movement in the direction toward or away from the native valve region, respectively. Rotational adjustment of the distal member 1052' in a first or second rotational direction (along arrows 1094 or 1096 respectively) permits rotational alignment of the valve prosthesis 101 within the native valve region.

Figure 11A:
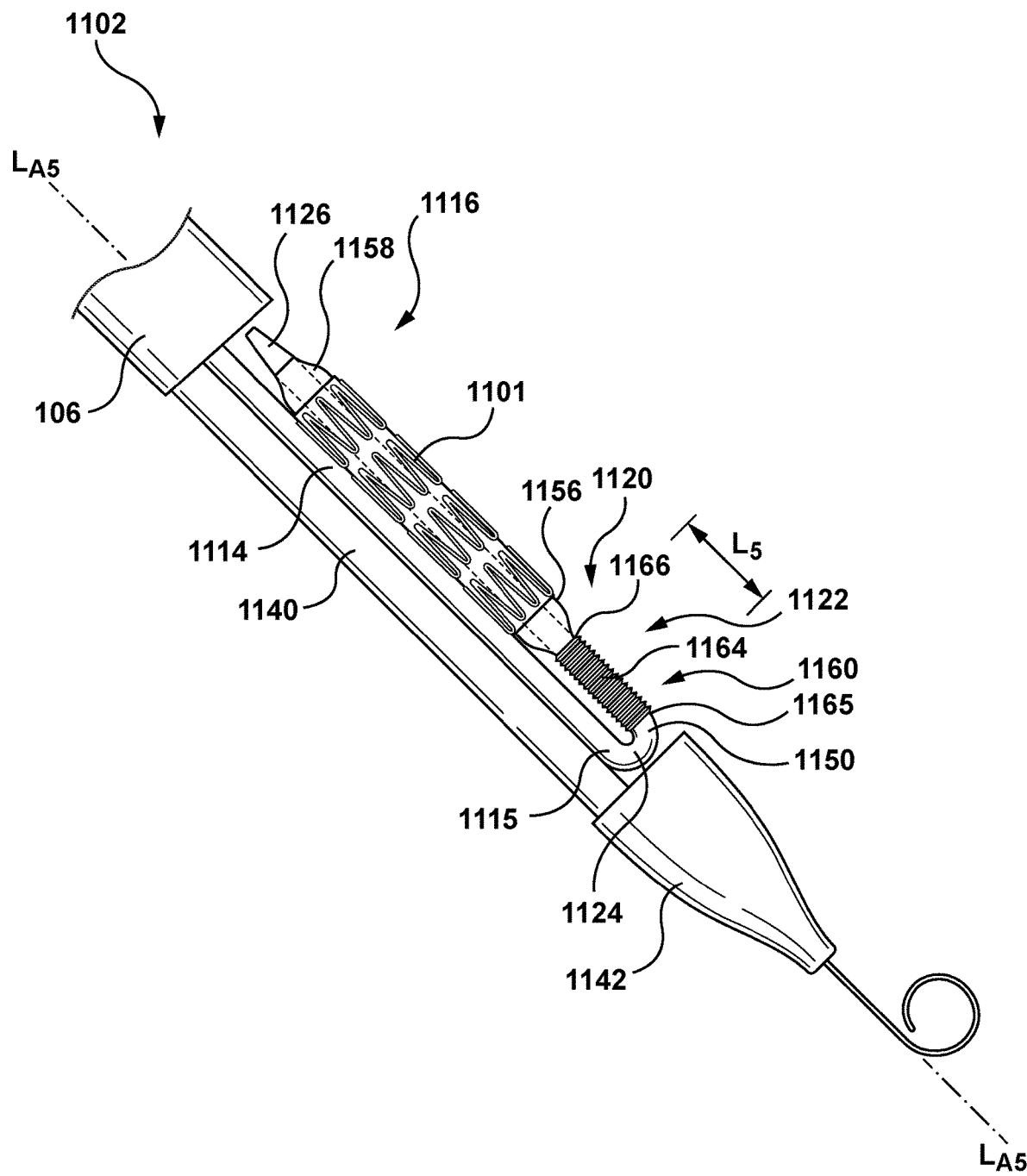
FIG. 11A is a partial side view of a distal segment of a delivery catheter for use with the heart valve prosthesis delivery system of FIG. 3 shown in a delivery configuration in accordance with yet another embodiment hereof.
Figure 11B:
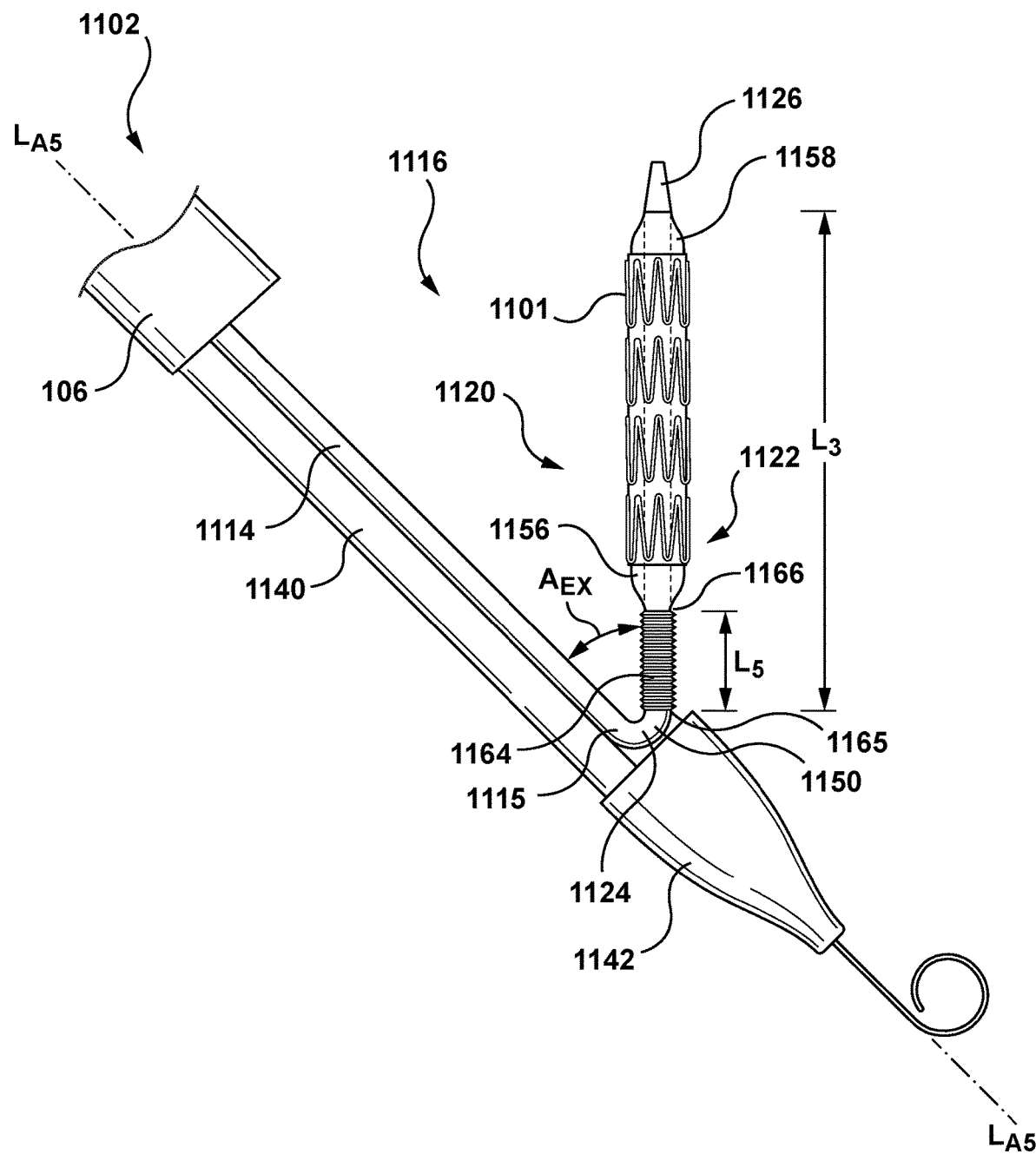
FIG. 11B is a partial side view of the delivery catheter of FIG. 11A shown in a partially deployed configuration in accordance with an embodiment hereof.
Figure 11C:
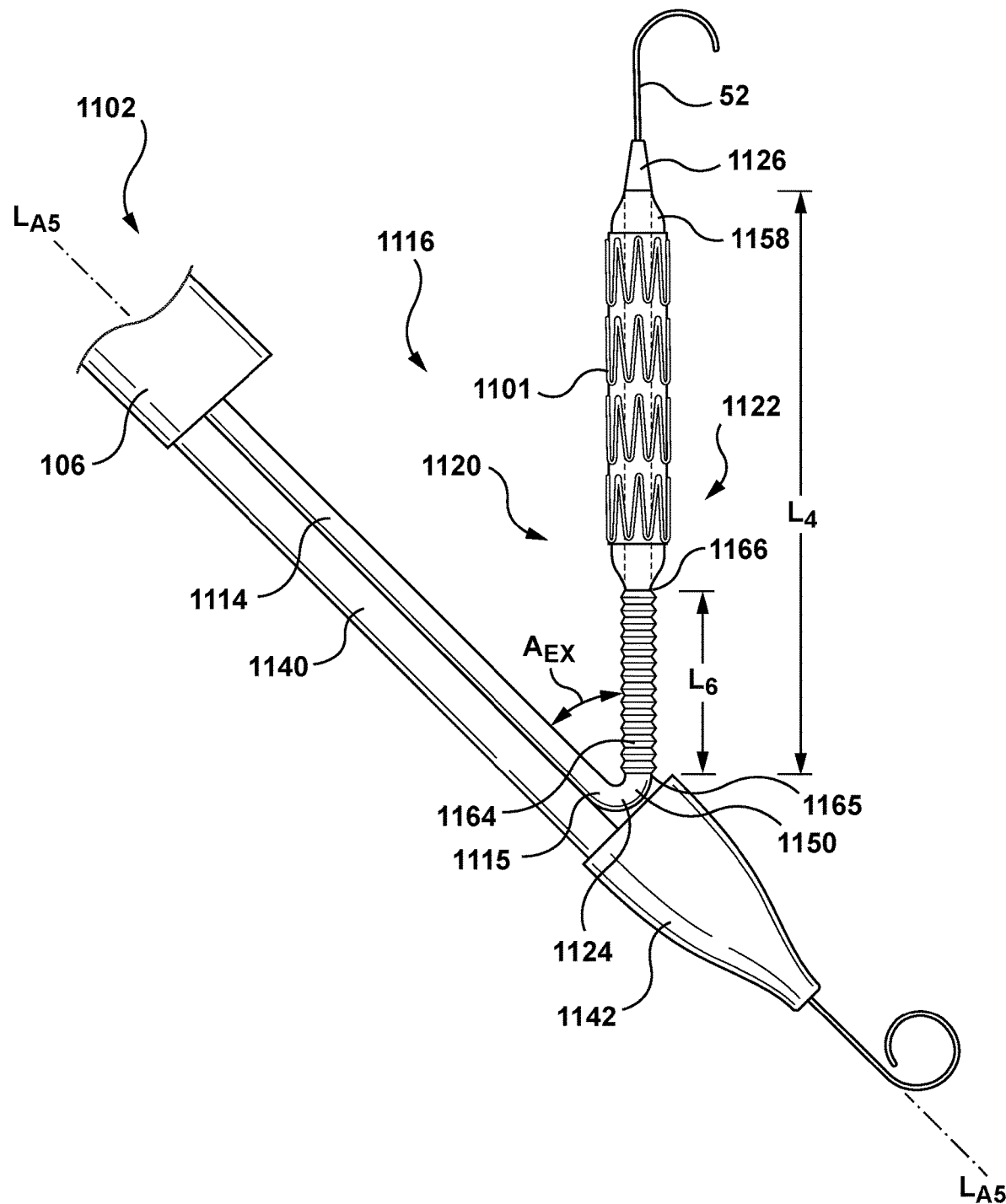
FIG. 11C is a partial side view of the delivery catheter of FIGS. 11A and 11B shown in a deployed configuration in accordance with an embodiment hereof.

FIGS. 11A-11C illustrate a distal segment 1116 of a delivery catheter 1102 for use with a heart valve prosthesis delivery system such as the delivery system 100 of FIG. 3 in accordance with a further embodiment hereof. Referring to FIGS. 11A-11C together, the delivery catheter 1102 includes features generally similar to the features of the delivery catheter 1002 described above with reference to FIGS. 10A-10C. For example, the delivery catheter 1102 includes a first tubular component 1114 and an articulation assembly 1120 at a distal end 1115 of the first tubular component 1114. The delivery catheter 1102 also include a second tubular component 1140 and a second atraumatic tip 1142 generally similar to the second tubular component 1040 and the second atraumatic tip 1042 of the delivery catheter 1002 (FIGS. 10A-10C).

Also similar to the delivery catheter 1002 (FIGS. 10A-10C), the delivery catheter 1102 partially deploys in a first phase from a delivery configuration (FIG. 11A) to a partially deployed configuration (FIG. 10B) in which an arm portion 1122 angles away from a longitudinal axis $L_{A5}$ of the first tubular component 1114 by an extension angle $A_{EX}$ (FIG. 11B) provided by an elbow portion 1124. The delivery catheter 1102 also deploys in a second phase by extending an arm portion length $L_3$ (FIG. 11B) to an extended length $L_4$ (FIG. 11C). However, the delivery catheter 1102 differs from the delivery catheter 1002 in that the delivery catheter 1102 does not include a separate inflation tubular member 1052 for extending a length $L_3$ of the arm portion 1122.

As shown in FIGS. 11A-11C, the arm portion 1122 includes a bellows connector 1164 at a proximal arm segment 1160. The bellows connector 1164 can be attached at a first end 1165 to an outermost tubular member 1150 and to a balloon 1156 at a second end 1166. In the first phase of deployment, the bellows connector 1164 is in a contracted state and has a length $L_5$ (FIGS. 11A and 11B). Inflation fluid provided by an external inflation fluid source 107 (FIG. 3) through a lumen (not shown) provided by the outermost tubular member 1150 increases a partial pressure within the proximal arm segment 1160, thereby extending the bellows connector 1164 to a length $L_6$ in an extended state (FIG. 11C). As the arm portion 1122 reaches or transforms to the extended state (e.g., having length $L_4$), the arm portion 1122 is moved into position within the native heart valve where continued and/or increased fluid flow from the inflation fluid source 107 (FIG. 3) inflates the balloon 1156 to expand and deploy the balloon-expandable prosthetic valve device 1101, which is carried over the balloon 1156 of the delivery catheter 1102. Alternatively, the arm portion 1122 can be moved toward and/or within the native valve region prior to providing pressurized fluid flow to extend the bellows connector 1164 (e.g., which would further advance the prosthetic valve device 1101 into a desired position). In one embodiment, the delivery catheter 1102 can include an innermost tubular member 1158 (shown in dashed lines) that extends from the handle component 104 (FIG. 3) of the delivery catheter 1102, through the balloon 1156 and, optionally, through a first atraumatic tip 1126 to provide a guidewire lumen (not shown) therethrough. Referring to FIG. 11C, a guidewire 52 can be received through the guidewire lumen to facilitate positioning of the balloon-expandable prosthetic valve device 1101 within a target heart valve during deployment.

Figure 12A:
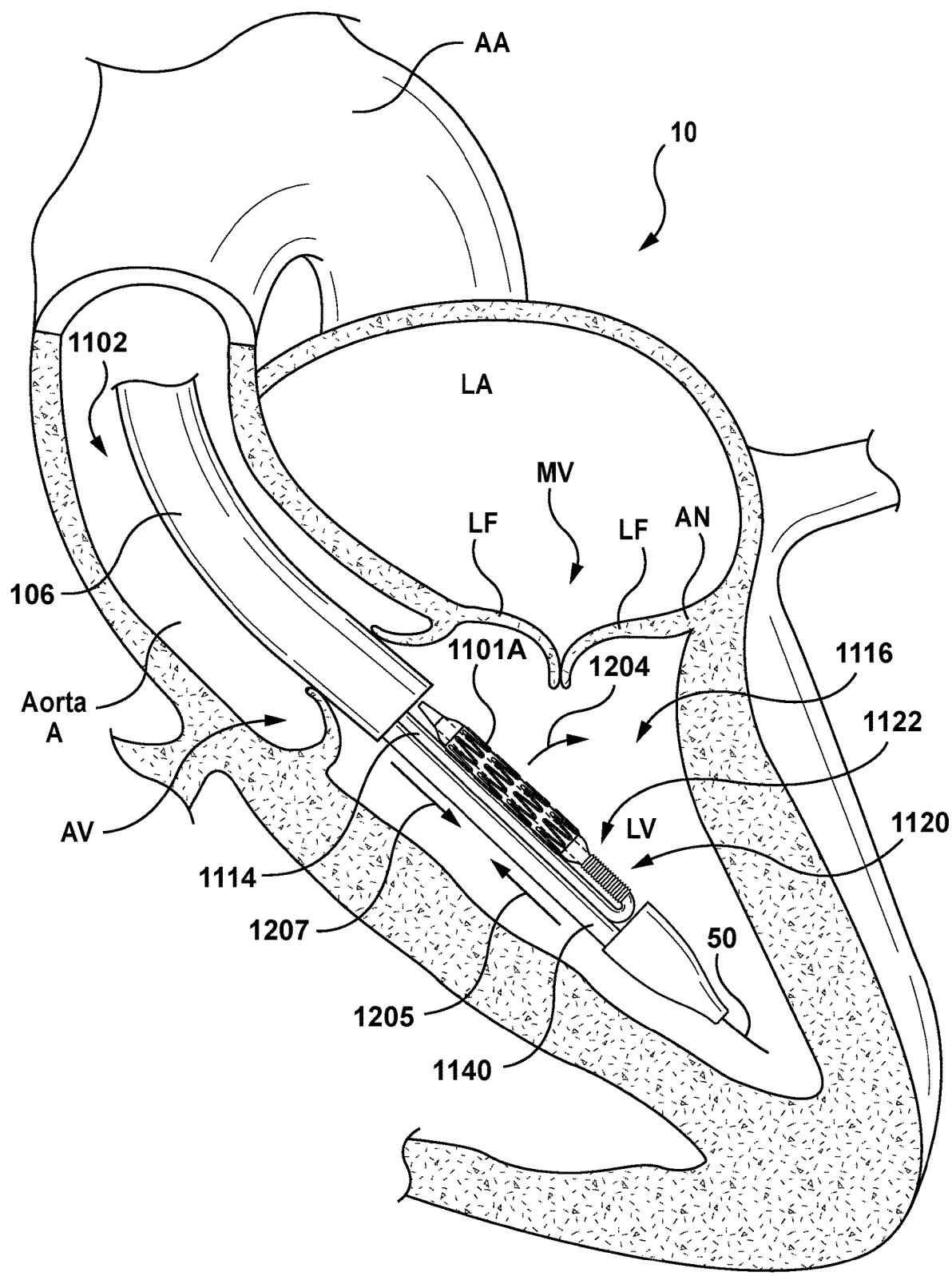
FIGS. 12A-12C are sectional cut-away views of the heart illustrating a method of delivering and positioning a mitral valve prosthesis using a retrograde approach in accordance with another embodiment hereof.
Figure 12B:
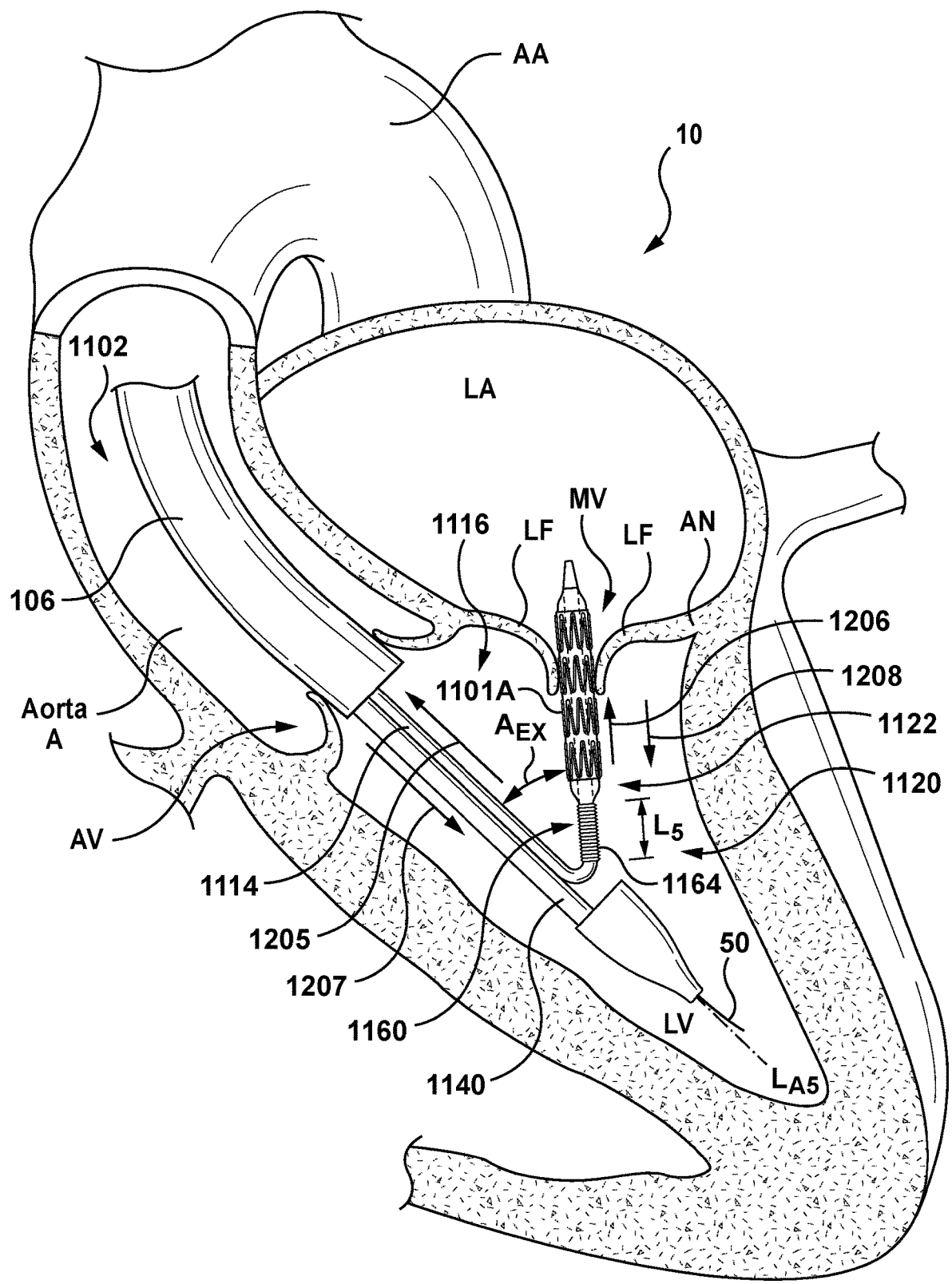
Figure 12C:
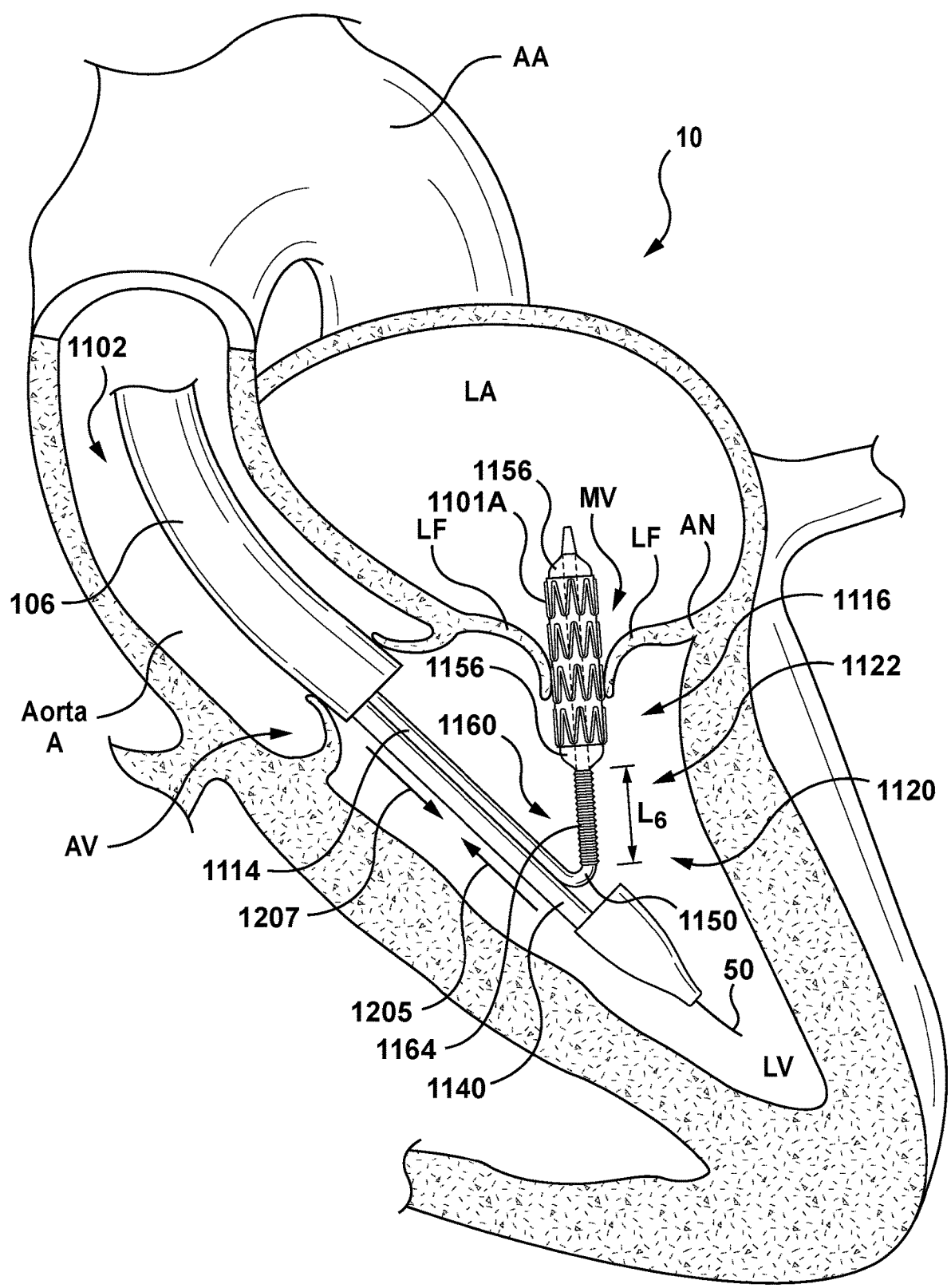

FIGS. 12A-12C are sectional cut-away views of the heart 10 illustrating a retrograde approach for delivering and positioning the balloon-expandable mitral valve prosthesis 1101A using the delivery catheter 1102 of FIGS. 11A-11C and in accordance with an embodiment hereof. Referring to FIGS. 12A-12C together, the distal segment 1116 of the delivery catheter 1102 is shown positioned in the left ventricle LV, and the outer tubular component 106 housing the first and second tubular components 1114, 1140 of the delivery catheter 1102 is shown in an intravascular path extending from the aortic arch AA, through the ascending aorta A, and crossing the aortic valve AV. As discussed above, intravascular access to the aortic arch AA and ascending aorta A can be achieved via a percutaneous access site in a femoral, brachial, radial, or axillary artery. Similar to the delivery catheter 102 shown in FIG. 3, the delivery catheter 1102 can include the handle component 104 coupled to a proximal segment (not shown) of the delivery catheter 1102 that is at least partially exposed externally of the patient as the distal segment 1116 of the delivery catheter 1102 carrying the mitral valve prosthesis 1101A is advanced to the left ventricle LV in the patient. By manipulating the handle component (not shown) of the delivery catheter 1102 from outside the vasculature, a clinician may advance the delivery catheter 1102 by remotely manipulating the distal segment 1116 of the delivery catheter 1102.

Referring back to FIGS. 12A-12C, the articulation assembly 1120 of the delivery catheter 1102 may be advanced into the left ventricle LV and positioned generally below (e.g., downstream of) the mitral valve MV. Optionally, and as shown in FIG. 12A, a guidewire 50 may be used over which the delivery catheter 1102 (e.g., via the second tubular component 1140) may be slidably advanced. Upon delivery of the articulation assembly 1120 to the left ventricle LV, the articulation assembly 1120 can be actuated (e.g., via tether device, push/pull wire, hydraulically, etc.) to move the arm portion 1122 in the direction of the arrow 1204 (FIG. 12A) such that the arm portion 1122 is angled away from the longitudinal axis $L_{AS}$ of the first tubular component 1114 (FIG. 12B). As illustrated in FIG. 12B, the extension angle $A_{EX}$ is less than 90° when orienting the mitral valve prosthesis 1101A with respect to the native mitral valve MV.

Referring to FIG. 12B, and in a next deployment step, the delivery catheter 1102 is partially retracted along the intravascular path (e.g., in the direction of arrow 1205) to bring the arm portion 1122 carrying the mitral valve prosthesis 1101A into proximity to and/or within the native mitral valve region (e.g., in apposition with the mitral valve annulus AN and/or leaflets LF). For example, movement of the delivery catheter 1102 in the proximal direction (along arrow 1205) translates to movement of the arm portion 1122 in the direction of arrow 1206 toward the mitral valve MV. Once the mitral valve prosthesis 1101A is positioned within or suitably near the mitral valve MV, and in a next step of deployment, the clinician can initiate pressurized fluid flow through the delivery catheter 1102 from the inflation fluid source 107 (FIG. 3).

As illustrated in FIG. 12C, inflation fluid provided by the external inflation fluid source 107 (FIG. 3), through a lumen (not shown) defined by the outermost tubular member 1150, increases a partial pressure within the proximal arm segment 1160, and transitions the bellows connector 1164 from the contracted state (FIG. 12B) having the length $L_5$ to the extended state (FIG. 12C) having the length $L_6$. Extension of the bellows connector 1164 further advances the mitral valve prosthesis 1101A into the mitral valve region while the delivery catheter 1102 otherwise remains stationary (e.g., stably positioned). As inflation fluid continues to flow through the delivery catheter 1102, the balloon 1156 expands and initiates outward expansion of the balloon-expandable frame of the mitral valve prosthesis 1101A within the native mitral valve region (shown in FIG. 12C).

During deployment, adjustment of the position of the mitral valve prosthesis 1101A with respect to the mitral valve MV, can be accomplished by manipulating the handle component (not shown) of the delivery catheter 1102 to incrementally advance and/or retract the distal segment 1116 of the delivery catheter 1102 to adjust the position of the arm portion 1122 within the left ventricle LV and/or within the mitral valve MV. Accordingly, a clinician can advance the delivery catheter 1102 in a distal direction (e.g., along arrow 1207) to move the arm portion 1122 in the direction of arrow 1208 when in the deployed state (e.g., further into the left ventricle LV) (FIG. 12B). Likewise, a clinician can retract the delivery catheter 1102 in a proximal direction (e.g., in the direction of arrow 1205) to move the arm portion 1122 in the deployed state (in the direction of arrow 1206) into the native mitral valve region (FIG. 12B). Referring to FIG. 12C, and while the mitral valve prosthesis 1101A is expanding by inflation of the balloon 1156, the operator can further control the placement of the mitral valve prosthesis 1101A within the mitral valve MV by incrementally advancing/retracting the delivery catheter 1102 as described.

As discussed above, image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery and positioning of the mitral valve prosthesis 1101A at the target native valve region. With reference to FIGS. 12A-12C together, a clinician can, in real time, determine a desired target point at which to position the mitral valve prosthesis 1101A within the mitral valve MV (e.g., at a center of the valve, at a region of leaflet coaptation, etc.) and retract and/or advance the delivery catheter 1102 to move the arm portion 1122 along arrows 1206 and/or 1208, respectively.

Following delivery, placement and implantation of the mitral valve prosthesis 1101A within the mitral valve MV (or other desired valve location), the articulation assembly 1120 can be withdrawn from the mitral valve MV by withdrawing inflation fluid from the delivery catheter 1101 to collapse the balloon 1156 and the bellows connector 1164, and by advancing the delivery catheter 1102 in the direction of arrow 1207. Once the arm portion 1122 is downstream of the mitral valve MV, the arm portion 1122 may be returned to the closed delivery state and the delivery catheter 1102 and remaining guidewire (if any) can be removed from the heart 10 and out of the body of the patient.

Additional Embodiments

Features of the heart valve delivery systems, delivery catheters and delivery catheter components described above and illustrated in FIGS. 3-12C can be modified to form additional embodiments configured in accordance herewith. For example, the delivery system 100 can provide delivery of any of the delivery catheters having articulation assemblies described and illustrated in FIGS. 4A-12C to a targeted heart region (e.g., left ventricle), and can further incorporate additional delivery elements such as straightening sheaths and/or guide wires controllable, for example, using the handle component 104. Similarly, the catheter assemblies described above having a first tubular component and a second tubular component, may only include the first tubular component. Furthermore, embodiments shown configured for carrying self-expanding prosthetic valve devices may also be configured to carry balloon-expandable prosthetic valve devices and vice versa. Additionally, catheter assemblies having only one guidewire lumen can be provided with more than one lumen.

Furthermore, while the delivery catheters described above are discussed as being suitable for delivering a mitral valve prosthesis to the native mitral valve using a retrograde approach, it will be understood that the delivery catheters may also be suitable for delivering heart valve devices for repair and/or replacement of other heart valves (e.g., pulmonary valve, tricuspid valve, etc.). Various arrangements of the delivery catheters described herein may also be used to deliver other therapeutic or medical tools within body lumens. For example, targeted and/or aligned delivery of intraluminal camera devices, surgical tools, two-part prosthetic devices such as a valve member with a separate docking member, etc. are contemplated with described articulation assemblies.

Various method steps described above for delivery and positioning of prosthetic valve devices (e.g., mitral valve prosthesis) within a native heart valve of a patient also can be interchanged to form additional embodiments of the present technology. For example, while the method steps described above are presented in a given order, alternative embodiments may perform steps in a different order. The various embodiments described herein may also be combined to provide further embodiments.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of deploying a mitral valve prosthesis, the method comprising:
   advancing a delivery catheter through an aortic arch in a retrograde manner, the delivery catheter including an articulation assembly having a movable arm portion, wherein during the advancing of the delivery catheter the articulation assembly is in a closed state in which the arm portion is substantially parallel to a longitudinal axis of the delivery catheter with the mitral valve prosthesis being releasably attached to the arm portion;
   positioning the articulation assembly in the left ventricle downstream of a native mitral valve;
   transitioning the articulation assembly from the closed state to an open state in which the arm portion is angled away from the longitudinal axis of the delivery catheter;
   positioning the arm portion and the mitral valve prosthesis releasably attached thereto within the native mitral valve; and
   deploying the mitral valve prosthesis within the native mitral valve.

2. The method of claim 1, wherein the articulation assembly includes an elbow portion having a shape-memory to bias the arm portion into the open state.

3. The method of claim 2, wherein a distal component of the delivery catheter includes a recess that receives the elbow portion therein to constrain the arm portion when the articulation assembly is in the closed state, and
   wherein transitioning the articulation assembly from the closed state to the open state includes distally advancing the distal component to release the arm portion and allow the arm portion to return to the open state.

4. The method of claim 1, wherein when the articulation assembly is in the closed state, an elbow portion of the articulation assembly is in a state of flexion in which an extension angle formed between the arm portion and the delivery catheter is substantially 0 degrees.

5. The method of claim 4, wherein when the articulation assembly is in the open state, the elbow portion is in a state of extension and positions the arm portion in an outwardly angled direction with respect to the longitudinal axis of the delivery catheter.

6. The method of claim 5, wherein in the state of extension, the extension angle formed between the arm portion and the delivery catheter is less than 90 degrees.

7. The method of claim 5, wherein the elbow portion includes a bellows connector having concertinaed sides, and wherein the elbow portion transitions between the state of flexion and the state of extension hydraulically.

8. The method of claim 5, wherein the elbow portion is a hinged joint, and wherein advancement of a wire relative to a remainder of the delivery catheter angles the arm portion away from the delivery catheter to transition the elbow portion from the state of flexion to the state of extension.

9. The method of claim 5, wherein the elbow portion includes a shape-memory to bias the arm portion into the open state.

10. The method of claim 9, wherein the delivery catheter further includes a tether device attached to the arm portion that restrains the arm portion in the closed state and wherein transitioning the articulation assembly from the closed state to an open state includes actuation of the tether device to allow the arm portion to return to the open state.

11. The method of claim 9, wherein the delivery catheter further includes a distal tip that restrains the arm portion in the closed state and wherein transitioning the articulation assembly from the closed state to an open state includes distally advancing the distal tip to release the arm portion and allow the arm portion to return to the open state.

12. The method of claim 1, wherein positioning the arm portion and the mitral valve prosthesis releasably attached thereto within the native mitral valve includes actuating a steering mechanism of the delivery catheter, the steering mechanism including a pull wire.

13. The method of claim 1, wherein positioning the arm portion and the mitral valve prosthesis releasably attached thereto within the native mitral valve includes distally advancing or proximally retracting the delivery catheter.

14. The method of claim 1, wherein positioning the arm portion and the mitral valve prosthesis releasably attached thereto within the native mitral valve includes adjusting an extension angle formed between the arm portion and the delivery catheter.

15. The method of claim 14, wherein adjusting the extension angle includes tensioning or relaxing a tether device attached to the arm portion.

16. The method of claim 1, wherein the mitral valve prosthesis is self-expanding and deploying the mitral valve prosthesis includes release of a cinch device.

17. The method of claim 1, wherein a balloon is attached to the arm portion of the articulation assembly.

18. The method of claim 17, wherein the mitral valve prosthesis is balloon-expandable and deploying the mitral valve prosthesis includes expanding the balloon to expand the mitral valve prosthesis.

19. The method of claim 17, wherein transitioning the articulation assembly from the closed state to the open state includes expanding the balloon.

20. The method of claim 1, further comprising:
returning the articulation assembly to the closed state after deploying the mitral valve prosthesis; and
proximally retracting the delivery system for removal.

* * * * *